US009334493B2

(12) United States Patent
Joergensen

(10) Patent No.: US 9,334,493 B2
(45) Date of Patent: May 10, 2016

(54) SELECTION OF WELL-EXPRESSED SYNTHETIC GENES

(75) Inventor: Steen Troels Joergensen, Allerød (DK)

(73) Assignee: Novozymes A/S, Bagsvaerd (DK)

( * ) Notice: Subject to any disclaimer, the term of this patent is extended or adjusted under 35 U.S.C. 154(b) by 1351 days.

(21) Appl. No.: 12/516,721

(22) PCT Filed: Dec. 20, 2007

(86) PCT No.: PCT/EP2007/064337
§ 371 (c)(1),
(2), (4) Date: Dec. 15, 2009

(87) PCT Pub. No.: WO2008/077881
PCT Pub. Date: Jul. 3, 2008

(65) Prior Publication Data
US 2010/0120623 A1  May 13, 2010

Related U.S. Application Data

(60) Provisional application No. 60/871,521, filed on Dec. 22, 2006, provisional application No. 60/908,748, filed on Mar. 29, 2007.

(30) Foreign Application Priority Data

Dec. 22, 2006  (DK) ................................. 2006 01698
Mar. 26, 2007  (EP) .................................... 07104896
Oct. 1, 2007  (EP) .................................... 07117672

(51) Int. Cl.
*C12N 15/67* (2006.01)
*C12N 15/10* (2006.01)

(52) U.S. Cl.
CPC ............ *C12N 15/1086* (2013.01); *C12N 15/67* (2013.01)

(58) Field of Classification Search
None
See application file for complete search history.

(56) References Cited

U.S. PATENT DOCUMENTS

2002/0187497 A1* 12/2002 Dasgupta et al. ................. 435/6
2008/0044853 A1*  2/2008 Jorgensen et al. ........... 435/69.1

FOREIGN PATENT DOCUMENTS

WO          00/42215 A1    7/2000
WO     WO 2005/123915     12/2005

OTHER PUBLICATIONS

Wells et al (1999 Transgenic Research 8:371-81).*
Sprengel et al., "Translationally Coupled Initiation of Protein Synthesis in *Bacillus subtilis*", Nucleic Acids Research, vol. 13 No. 3, pp. 893-909 (1985).
Ishida et al., "Effective Structure of a Leader Open Reading Frame for Enhancing the Expression of GC-rich Genes", Journal of Biochemistry, vol. 132, No. 1, pp. 63-70 (2002).
Wu et al., "SGDB: A Database of Synthetic Genes Re-Designed for Optimizing Protein Over-Expression", Nucleic Acids Research, vol. 35, pp. D76-D79 (2006).
Zaghloul et al., "Translational Coupling in *Bacillus subtilis* of a Heterologous *Bacillus Subtilis-Escherichia coli* Gene Fusion", Journal of Bacteriology, vol. 164, No. 2, pp. 550-555 (1985).
Peijnenburg et al., "Translational Coupling in a Penp-Lacz Gene Fusion in *Bacillus subtilis* and *Escherichia coli*", Molecular and General Genetics, vol. 221, No. 2, pp. 267-272 (1990).
Kojima et al., "Eukaryotic Translational Coupling in Uaaug Stop-Start Codons for the Bicistronic RNA Translation of the Non-Long Terminal Repeat Retrotransposon SART1", Molecular and Cellular Biology, vol. 25, No. 17, pp. 7675-7686 (2005).

* cited by examiner

*Primary Examiner* — Christopher M Gross
(74) *Attorney, Agent, or Firm* — Elias Lambiris

(57) ABSTRACT

The invention relates to a method of indirectly identifying a polynucleotide comprising an open reading frame having an improved expression level from a library of polynucleotides encoding the same polypeptide of interest, or variants or homologues thereof, in a host cell expression library, the method comprising the steps of: a) providing an expression library in a host cell, said library comprising at least two different open reading frames encoding the same polypeptide of interest, or variants or homologues thereof, each open reading frame being translationally coupled to a downstream gene encoding a screenable or selectable reporter; b) culturing the host cell under conditions conducive to the expression of the polypeptide of interest, or variant or homologue thereof; and c) screening and/or selecting for a host cell having an improved expression level of the translationally coupled reporter when compared to one or more other host cells of the library, thus indirectly identifying a polynucleotide comprising an open reading frame having an improved expression level in the host cell; as well as the expression libraries and host cells comprising said libraries.

19 Claims, 9 Drawing Sheets

SEQUENCE LISTING

<160> NUMBER OF SEQ ID NOS: 39

<210> SEQ ID NO 1
<211> LENGTH: 21
<212> TYPE: DNA
<213> ORGANISM: Artificial sequence
<220> FEATURE:
<223> OTHER INFORMATION: Primer PEP1

<400> SEQUENCE: 1
tatcttgaaa ggagggatgc c     21

<210> SEQ ID NO 2
<211> LENGTH: 80
<212> TYPE: DNA
<213> ORGANISM: Artificial sequence
<220> FEATURE:
<223> OTHER INFORMATION: Primer #431991

<400> SEQUENCE: 2
gactacgcgt tatgttctaa gtcttactcc ccaagaattg accatcggag tgacttcttg     60
gtagaacgtt gtgccacctg     80

<210> SEQ ID NO 3
<211> LENGTH: 38
<212> TYPE: DNA
<213> ORGANISM: Artificial sequence
<220> FEATURE:
<223> OTHER INFORMATION: Downstream reading primer

<400> SEQUENCE: 3
gagctagcgc atgcgtctca cttccttact gcgtctgg     38

```
<210> SEQ ID NO 4
<211> LENGTH: 25
<212> TYPE: DNA
<213> ORGANISM: Artificial sequence
<220> FEATURE:
<223> OTHER INFORMATION: Upstream reading primer

<400> SEQUENCE: 4
tgcggtacct gatctagatc tcggg                                            25

<210> SEQ ID NO 5
<211> LENGTH: 25
<212> TYPE: DNA
<213> ORGANISM: Artificial sequence
<220> FEATURE:
<223> OTHER INFORMATION: Downstream reading primer

<400> SEQUENCE: 5
cgagatctag atcaggtacc gcaac                                            25

<210> SEQ ID NO 6
<211> LENGTH: 43
<212> TYPE: DNA
<213> ORGANISM: Artificial sequence
<220> FEATURE:
<223> OTHER INFORMATION: Upstream reading primer

<400> SEQUENCE: 6
gactgaattc aattaagctt aacattaata attcttcaat tgc                        43

<210> SEQ ID NO 7
<211> LENGTH: 33
<212> TYPE: DNA
<213> ORGANISM: Artificial sequence
<220> FEATURE:
<223> OTHER INFORMATION: Downstream reading primer

<400> SEQUENCE: 7
gactggatcc ggttcgcgtc cggacagcac atc                                   33

<210> SEQ ID NO 8
<211> LENGTH: 37
<212> TYPE: DNA
<213> ORGANISM: Artificial sequence
<220> FEATURE:
<223> OTHER INFORMATION: Upstream reading primer

<400> SEQUENCE: 8
gactgcatgc ggccgctttt tcaccacagc accagcc                               37

<210> SEQ ID NO 9
<211> LENGTH: 33
<212> TYPE: DNA
<213> ORGANISM: Artificial sequence
<220> FEATURE:
<223> OTHER INFORMATION: Primer cat gene

<400> SEQUENCE: 9
atgaacttta ataaaattga tttagacaat tgg                                   33

<210> SEQ ID NO 10
<211> LENGTH: 44
<212> TYPE: DNA
<213> ORGANISM: Artificial sequence
<220> FEATURE:
<223> OTHER INFORMATION: Upstream cat reading primer
```

<400> SEQUENCE: 10
gactaagctt acgcgttata aaagccagtc attaggccta tctg         44

<210> SEQ ID NO 11
<211> LENGTH: 25
<212> TYPE: DNA
<213> ORGANISM: Artificial sequence
<220> FEATURE:
<223> OTHER INFORMATION: Downstream reading primer

<400> SEQUENCE: 11
agcgtgagct atcctgaagg taccg         25

<210> SEQ ID NO 12
<211> LENGTH: 57
<212> TYPE: DNA
<213> ORGANISM: Artificial sequence
<220> FEATURE:
<223> OTHER INFORMATION: Upstream 10R_pSJ6074 gene SOE primer

<400> SEQUENCE: 12
ccaattgtct aaatcaattt tattaaagtt catgtacgga gtctaactcc ccaagag         57

<210> SEQ ID NO 13
<211> LENGTH: 60
<212> TYPE: DNA
<213> ORGANISM: Artificial sequence
<220> FEATURE:
<223> OTHER INFORMATION: Upstream 10R_pSJ7802 gene SOE primer

<400> SEQUENCE: 13
ccaattgtct aaatcaattt tattaaagtt catgttctaa gtcttactcc ccaagaattg         60

<210> SEQ ID NO 14
<211> LENGTH: 100
<212> TYPE: DNA
<213> ORGANISM: Artificial sequence
<220> FEATURE:
<223> OTHER INFORMATION: Degenerate primer
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t

```
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t

<400> SEQUENCE: 14
ccaattgtct aaatcaattt tattaaagtt catgtncgna gncgnacncc ccangarttn      60
accatnggng tnacytcytg gtagaacgtt gtgccacctg                          100

<210> SEQ ID NO 15
<211> LENGTH: 58
<212> TYPE: DNA
<213> ORGANISM: Artificial sequence
<220> FEATURE:
<223> OTHER INFORMATION: Upstream 10R_pSJ6074 gene SOE primer #535797

<400> SEQUENCE: 15
ccaattgtct aaatcaattt tattaaagtt catcgcgtta tgtacggagt ctaactcc       58

<210> SEQ ID NO 16
<211> LENGTH: 61
<212> TYPE: DNA
<213> ORGANISM: Artificial sequence
<220> FEATURE:
<223> OTHER INFORMATION: Upstream 10R_pSJ6074 gene SOE primer #535798

<400> SEQUENCE: 16
ccaattgtct aaatcaattt tattaaagtt catagcacgc gttatgtacg gagtctaact     60
c                                                                    61

<210> SEQ ID NO 17
<211> LENGTH: 45
<212> TYPE: DNA
<213> ORGANISM: Artificial sequence
<220> FEATURE:
<223> OTHER INFORMATION: Downstream reading primer #289358

<400> SEQUENCE: 17
gactaagctt ctgcagcagc ggcggctact ggagcattac ctcag                    45

<210> SEQ ID NO 18
<211> LENGTH: 58
<212> TYPE: DNA
<213> ORGANISM: Artificial sequence
<220> FEATURE:
<223> OTHER INFORMATION: Upstream 10R_pSJ7802 gene SOE primer #542633

<400> SEQUENCE: 18
ccaattgtct aaatcaattt tattaaagtt catcgcgtta tgttctaagt cttactcc       58

<210> SEQ ID NO 19
<211> LENGTH: 14
<212> TYPE: DNA
<213> ORGANISM: Artificial sequence
<220> FEATURE:
<223> OTHER INFORMATION: 14 basepair region.

<400> SEQUENCE: 19
cgcgtgctag cggc                                                      14

<210> SEQ ID NO 20
```

```
<211> LENGTH: 57
<212> TYPE: DNA
<213> ORGANISM: Artificial sequence
<220> FEATURE:
<223> OTHER INFORMATION: Upstream 10R_pSJ6074 gene SOE primer #535799

<400> SEQUENCE: 20
ccaattgtct aaatcaattt tattaaagtt catgccgcta gcacgcgtta tgtacgg        57

<210> SEQ ID NO 21
<211> LENGTH: 57
<212> TYPE: DNA
<213> ORGANISM: Artificial sequence
<220> FEATURE:
<223> OTHER INFORMATION: Upstream 10R_pSJ7802 gene SOE primer #542634

<400> SEQUENCE: 21
ccaattgtct aaatcaattt tattaaagtt catgccgcta gcacgcgtta tgttcta        57

<210> SEQ ID NO 22
<211> LENGTH: 108
<212> TYPE: DNA
<213> ORGANISM: artificial sequence
<220> FEATURE:
<223> OTHER INFORMATION: Degenerate primer #550951
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t

<400> SEQUENCE: 22
ccaattgtct aaatcaattt tattaaagtt catcgcgtta tgtncgnagn cgnacncccc     60
angarttnac catnggngtn acytcytggt agaacgttgt gccacctg                 108

<210> SEQ ID NO 23
<211> LENGTH: 22
```

-continued

```
<212> TYPE: DNA
<213> ORGANISM: artificial sequence
<220> FEATURE:
<223> OTHER INFORMATION: Primer #410250

<400> SEQUENCE: 23
cacgatgggt ggtcgctgca gc                                              22

<210> SEQ ID NO 24
<211> LENGTH: 23
<212> TYPE: DNA
<213> ORGANISM: artificial sequence
<220> FEATURE:
<223> OTHER INFORMATION: Primer #538513

<400> SEQUENCE: 24
gtcgtttgtt ggttcaaata atg                                             23

<210> SEQ ID NO 25
<211> LENGTH: 53
<212> TYPE: DNA
<213> ORGANISM: artificial sequence
<220> FEATURE:
<223> OTHER INFORMATION: pSJ6074 from table 3.

<400> SEQUENCE: 25
accaggaagt gacaccgatg gtgaactctt ggggagttag actccgtaca taa            53

<210> SEQ ID NO 26
<211> LENGTH: 53
<212> TYPE: DNA
<213> ORGANISM: artificial sequence
<220> FEATURE:
<223> OTHER INFORMATION: SJ9019 from table 3.

<400> SEQUENCE: 26
accaggaggt gacccctatg gtaaactcat ggggcgtgcg gctacgcaca taa            53

<210> SEQ ID NO 27
<211> LENGTH: 53
<212> TYPE: DNA
<213> ORGANISM: artificial sequence
<220> FEATURE:
<223> OTHER INFORMATION: SJ9020 from table 3.

<400> SEQUENCE: 27
accaggaagt cactcctatg gtgaactcgt gggggggtccg cctccgaaca taa           53

<210> SEQ ID NO 28
<211> LENGTH: 53
<212> TYPE: DNA
<213> ORGANISM: artificial sequence
<220> FEATURE:
<223> OTHER INFORMATION: SJ9021 from table 3.

<400> SEQUENCE: 28
accaagaagt gacgccaatg gtgaactctt ggggcgttcg actccgtaca taa            53

<210> SEQ ID NO 29
<211> LENGTH: 53
<212> TYPE: DNA
<213> ORGANISM: artificial sequence
<220> FEATURE:
<223> OTHER INFORMATION: SJ9028 from table 3.

<400> SEQUENCE: 29
```
accaagaagt aacgcctatg gttaactctt ggggtgttcg gctacgaaca taa    53

<210> SEQ ID NO 30
<211> LENGTH: 53
<212> TYPE: DNA
<213> ORGANISM: artificial sequence
<220> FEATURE:
<223> OTHER INFORMATION: SJ9030 from table 3.

<400> SEQUENCE: 30
accaagaggt tactccaatg gtaaactcct ggggagtgcg actccggaca taa    53

<210> SEQ ID NO 31
<211> LENGTH: 53
<212> TYPE: DNA
<213> ORGANISM: artificial sequence
<220> FEATURE:
<223> OTHER INFORMATION: SJ9032 from table 3.

<400> SEQUENCE: 31
accaggaagt aaccccatg gttaactcgt ggggagtgcg actccggaca taa    53

<210> SEQ ID NO 32
<211> LENGTH: 53
<212> TYPE: DNA
<213> ORGANISM: artificial sequence
<220> FEATURE:
<223> OTHER INFORMATION: SJ9033 from table 3.

<400> SEQUENCE: 32
accaggaagt cacgcccatg gttaactctt ggggcgttcg ccttcggaca taa    53

<210> SEQ ID NO 33
<211> LENGTH: 53
<212> TYPE: DNA
<213> ORGANISM: artificial sequence
<220> FEATURE:
<223> OTHER INFORMATION: SJ9037 from table 3.

<400> SEQUENCE: 33
accaagaagt gactccaatg gtaaattctt ggggcgttcg acttcgaaca taa    53

<210> SEQ ID NO 34
<211> LENGTH: 53
<212> TYPE: DNA
<213> ORGANISM: artificial sequence
<220> FEATURE:
<223> OTHER INFORMATION: SJ9044 from table 3.
<220> FEATURE:
<221> NAME/KEY: misc_feature
<222> LOCATION: (46)..(46)
<223> OTHER INFORMATION: n is a, c, g, or t

<400> SEQUENCE: 34
accaggaagt tacacccatg gtcaactcat ggggagtccg gcttcngaca taa    53

<210> SEQ ID NO 35
<211> LENGTH: 53
<212> TYPE: DNA
<213> ORGANISM: artificial sequence
<220> FEATURE:
<223> OTHER INFORMATION: SJ9047 from table 3.

<400> SEQUENCE: 35
accaagaggt aacgcctatg gttaattcat ggggcgtccg gctgcgtaca taa    53

-continued

```
<210> SEQ ID NO 36
<211> LENGTH: 53
<212> TYPE: DNA
<213> ORGANISM: artificial sequence
<220> FEATURE:
<223> OTHER INFORMATION: SJ9054 from table 3.

<400> SEQUENCE: 36
accaagaggt tactcccatg gtaaactctt gggggtccg gctgcgtaca taa          53

<210> SEQ ID NO 37
<211> LENGTH: 53
<212> TYPE: DNA
<213> ORGANISM: artificial sequence
<220> FEATURE:
<223> OTHER INFORMATION: SJ9057 from table 3.

<400> SEQUENCE: 37
accaagaggt caccccaatg gttaattctt gggggtccg tcttcgcaca taa          53

<210> SEQ ID NO 38
<211> LENGTH: 53
<212> TYPE: DNA
<213> ORGANISM: artificial sequence
<220> FEATURE:
<223> OTHER INFORMATION: SJ9059 from table 3.

<400> SEQUENCE: 38
accaagaggt gactcctatg gttaactcgt ggggagttcg gctccgcaca taa          53

<210> SEQ ID NO 39
<211> LENGTH: 53
<212> TYPE: DNA
<213> ORGANISM: artificial sequence
<220> FEATURE:
<223> OTHER INFORMATION: Primer complementary
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
```

```
<221> NAME/KEY: misc_feature
<222> LOCATION: (47)..(47)
<223> OTHER INFORMATION: n is a, c, g, or t

<400> SEQUENCE: 39
tggtyctyca ntgnggntac canttragna ccccncangc ngangcntgt att            53
```

SELECTION OF WELL-EXPRESSED SYNTHETIC GENES

REFERENCE TO SEQUENCE LISTING

This application contains a Sequence Listing in computer readable form. The computer readable form is incorporated herein by reference.

CROSS-REFERENCE TO RELATED APPLICATIONS

This application is a 35 U.S.C. 371 national application of PCT/EP2007/064337 filed Dec. 20, 2007, which claims priority or the benefit under 35 U.S.C. 119 of Danish application no. PA 2006 01698 filed Dec. 22, 2006, European application nos. 07104896.1 filed Mar. 26, 2007 and 07117672.1 filed Oct. 1, 2007, and U.S. provisional application nos. 60/871,521 filed Dec. 22, 2006, and 60/908,748 filed Mar. 29, 2007 the contents of which are fully incorporated herein by reference.

SEQUENCE LISTING

This application comprises a sequence listing.

FIELD OF THE INVENTION

The present invention relates to a method of indirectly identifying a polynucleotide comprising an open reading frame having an improved expression level from a library of polynucleotides encoding the same polypeptide of interest, or variants or homologues thereof, in a host cell expression library, the method comprising the steps of:
  a) providing an expression library in a host cell, said library comprising at least two different open reading frames encoding the same polypeptide of interest, or variants or homologues thereof, each open reading frame being translationally coupled to a downstream gene encoding a screenable or selectable reporter;
  b) culturing the host cell under conditions conducive to the expression of the polypeptide of interest, or variant or homologue thereof; and
  c) screening and/or selecting for a host cell having an improved expression level of the translationally coupled reporter when compared to one or more other host cells of the library, thus indirectly identifying a polynucleotide comprising an open reading frame having an improved expression level in the host cell; as well as the expression libraries and host cells comprising said libraries.

BACKGROUND OF THE INVENTION

An increasing number of naturally existing genes have been redesigned at the nucleotide level and synthesized in attempts to improve protein yields (Wu, G., Zheng, Y., Qureshi, I., Zin, H. T., Beck, T., Bulka, B., Freeland, S. J. (2006) SGDB: a database of synthetic genes re-designed for optimizing protein over-expression. Nucleic Acids Research, 2006, vol. 00, Database issue D1-D4 (Nucleic Acids Research Advance Access published Nov. 7, 2006)).

Basically all methods for design of synthetic genes rely on some sort of codon optimization, which requires an understanding of what an optimal codon is, usually based on the general idea that translationally optimal codons are those which match the most abundant tRNA species in a host cell. A number of different companies today offer synthetic gene synthesis, where they frequently contribute with one or more other ideas about gene optimization, such as mRNA structure, mRNA stability, or codon context.

Codon usage in a host cell relative to the abundance of tRNA species therein is one of the clearly distinguishing sequence features that contribute to different levels of gene expression. However, in a database of synthetic genes from published, peer-reviewed studies, more than 20% of the genes did not increase protein yield after supposed codon optimization. It has been said that this figure of 20% negative optimization results is probably an underestimate of the problems in synthetic gene design, as peer-reviewed publications are likely to be biased towards reports of success (Wu et al., 2006; see above).

It has also been stated that a weakness of the current synthetic gene database is the lack of studies, where multiple versions of a synthetic gene have been designed to directly compare algorithms for codon optimization, and the paper advocates for research providing data of multiple variations in coding strategy for a single protein product (Wu et al., 2006; see above).

The term "translational coupling" describes the observation, that translational initiation can be affected by translational termination events close to the initiation codon, in particular the observation that translation termination enhances translation initiation of closely associated genes (Sprengel, R., Reiss, B., Schaller, H. (1985). Translationally coupled initiation of protein synthesis in *Bacillus subtilis*. Nucleic Acids Research, 13, 893-909, and references therein).

Translational coupling can be made solely responsible for translation of a specific open reading frame, as described in the study by Sprengel et al., 1985. They constructed various combinations of the *B. licheniformis* penP gene and the Tn5 neo gene, and investigated the expression of these constructs in *B. subtilis*. The Tn5 neo gene, in the absence of translational coupling, was not expressed in *B. subtilis*. The study found that different amounts of neo gene product were produced from constructs that differed in the distance between the penP termination and the neo initiation codon, and found that activation of neo gene expression was highest if the neo ATG start codon overlapped with the TGA termination codon of the penP reading unit in the sequence ATGA. The study concluded that sequences immediately in front of the initiation codon of the translationally coupled gene are not involved in the initiation reaction following translational termination. The study estimated the frequency of ribosomes reinitiating at the neo initiation codon overlapping with the termination codon in the sequence ATGA to 5-10%, for some specific constructs.

The Sprengel study further used the translational coupling phenomenon as a tool to investigate the expression and regulation of the *B. licheniformis* penP gene in *B. licheniformis* itself, and mentions its use for stabilizing highly instable penP gene derivatives.

Another publication (Zaghloul, T. I., Kawamura, F., Doi, R. H. (1985). Translational coupling in *Bacillus subtilis* of a heterologous *Bacillus subtilis-Escherichia coli* gene fusion. Journal of Bacteriology, 164, 550-555) reports that expression of a Tn9-derived cat gene in *B. subtilis* was dependent on a gene fusion, wherein translation initiated at the *B. subtilis* aprA gene and terminating within the cat ribosome binding site was responsible for translation initiation of the cat gene.

Peijnenburg et al. (Peijnenburg, A. A. C. M., Venema, G., Bron, S. (1990). Translational coupling in a penP-lacZ gene fusion in *Bacillus subtilis* and *Escherichia coli*. Use of AUA as a restart codon. Molecular and General Genetics, 221, 267-272) describes a situation, in which translation of the *E. coli* lacZ gene is dependent on translation of an upstream *B. licheniformis* penP gene fragment, the genes being fused so that the stop codon (TAG) of the penP gene fragment overlaps a putative start codon (ATA) for the lacZ gene. Use of this particular codon for initiation was confirmed by N-terminal amino acid sequencing of the produced lacZ gene product.

Kojima et al. (Kojima, K. K. et al. (2005) Eukaryotic Translational Coupling in UAAUG Stop-Start Codons for the Bicistronic RNA Translation of the Non-Long Terminal Repeat Retrotransposon SART1, Molecular and Cellular Biology, 25(17): 7675-7686) discloses translational coupling in a eukaryotic system.

It has been our experience with synthetic gene design that different genes encoding the same protein product, and designed according to the same (or at least very similar) codon optimization rules, have resulted in genes giving significantly different protein yields when inserted into the desired expression organism, yield differences for which we currently have no explanation.

There is therefore a strong need for methods for rapid and efficient identification of those synthetic genes that give high protein yields.

SUMMARY OF THE INVENTION

The computational methods for gene design of today in our experience give variable and unpredictable results. In contrast, the present invention provides a method for screening or selecting the well-expressed genes in an expression library comprising a multitude of different synthetic genes encoding the same protein, based on their expression characteristics. An interesting aspect of the invention lies in its combination with well-known variant- or homologue-screening techniques, thereby instantly providing those open reading frames that encode functional variants or homologues thereof, which are efficiently expressed.

The invention is based on the production of the desired gene-product being translationally coupled to the production of a cell-associated, selectable or easily screenable marker.

Accordingly, in a first aspect the invention relates to a method of indirectly identifying a polynucleotide comprising an open reading frame having an improved expression level from a library of polynucleotides encoding the same polypeptide of interest, or variants or homologues thereof, in a host cell expression library, the method comprising the steps of:

a) providing an expression library in a host cell, said library comprising at least two different open reading frames encoding the same polypeptide of interest, or variants or homologues thereof, each open reading frame being translationally coupled to a downstream gene encoding a screenable or selectable reporter;

b) culturing the host cell under conditions conducive to the expression of the polypeptide of interest, or variant or homologue thereof; and c) screening and/or selecting for a host cell having an improved expression level of the translationally coupled reporter when compared to one or more other host cells of the library, thus indirectly identifying a polynucleotide comprising an open reading frame having an improved expression level in the host cell.

In a second aspect, the invention relates to an expression library comprising at least two different open reading frames encoding the same polypeptide of interest, or variants or homologues thereof, each encoding open reading frame being translationally coupled to a downstream gene encoding a screenable or selectable reporter.

A final aspect of the invention relates to a host cell comprising an expression library as defined in the second aspect.

DEFINITIONS

Figure 1:
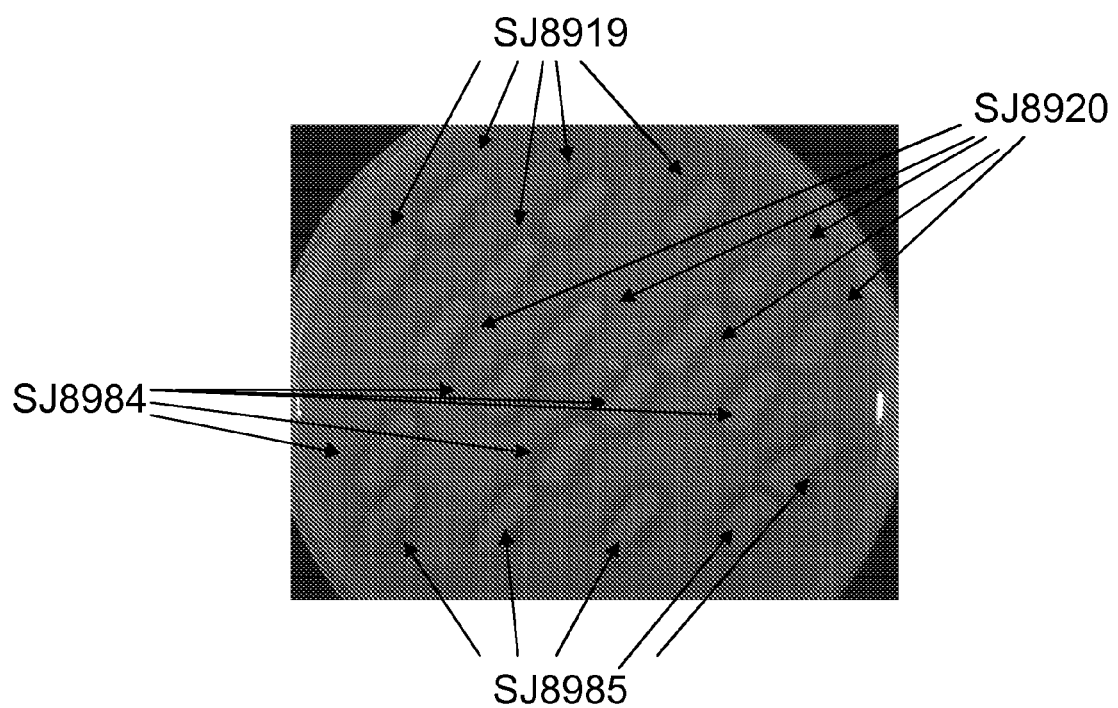
FIG. 1 shows how the strains were streaked: The first 5 streaks were from SJ8919 (for the 4 bp spacing constructs) or from SJ8923 (14 bp spacing). The following 5 streaks were from SJ8920 (4 bp spacing) or from SJ8924 (14 bp spacing). The next 5 streaks were from SJ8984 (4 bp spacing) or from SJ8986 (14 bp spacing). The final 5 streaks were from SJ8985 (4 bp spacing) or from SJ8987 (14 bp spacing).
Figure 2A:
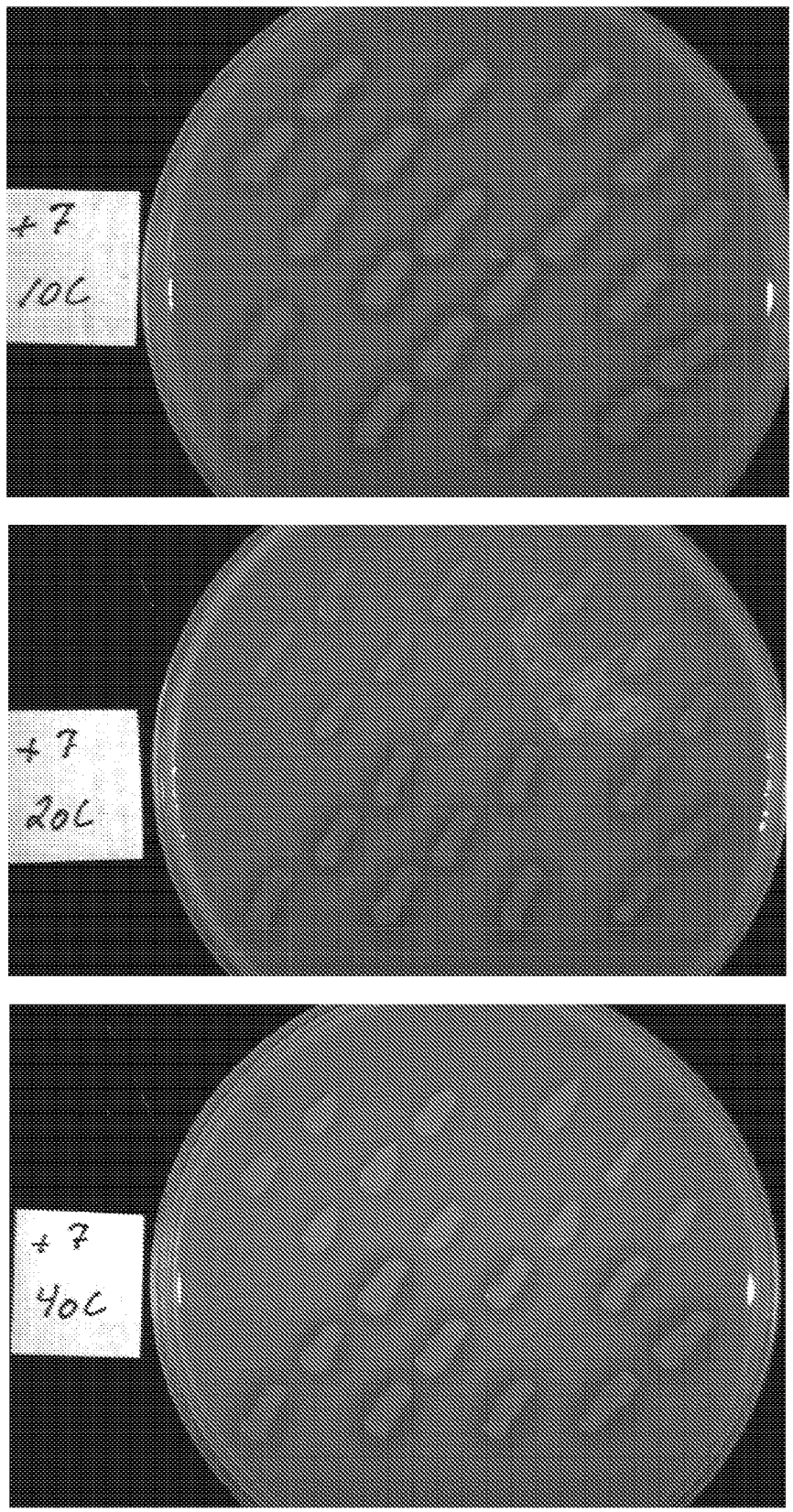
FIGS. 2A and 2B show testing of the 4 bp spacing constructs. The labelling is interpreted as follows: The "+7" indicates that it is the 4 bp spacing constructs. "10C" indicates that the plate contains 10 microgram/ml chloramphenicol, "200" indicates it contains 20 microgram/ml chloramphenicol etc., up to 100 microgram/ml chloramphenicol. It is evident that strains SJ8984 and SJ8985, containing the high-yielding synthetic gene 10R_pSJ7802 are significantly more resistant to chloramphenicol than the strains SJ8919 and SJ8920, which contain the low-yielding synthetic gene 10R_pSJ6074.
Figure 2B:
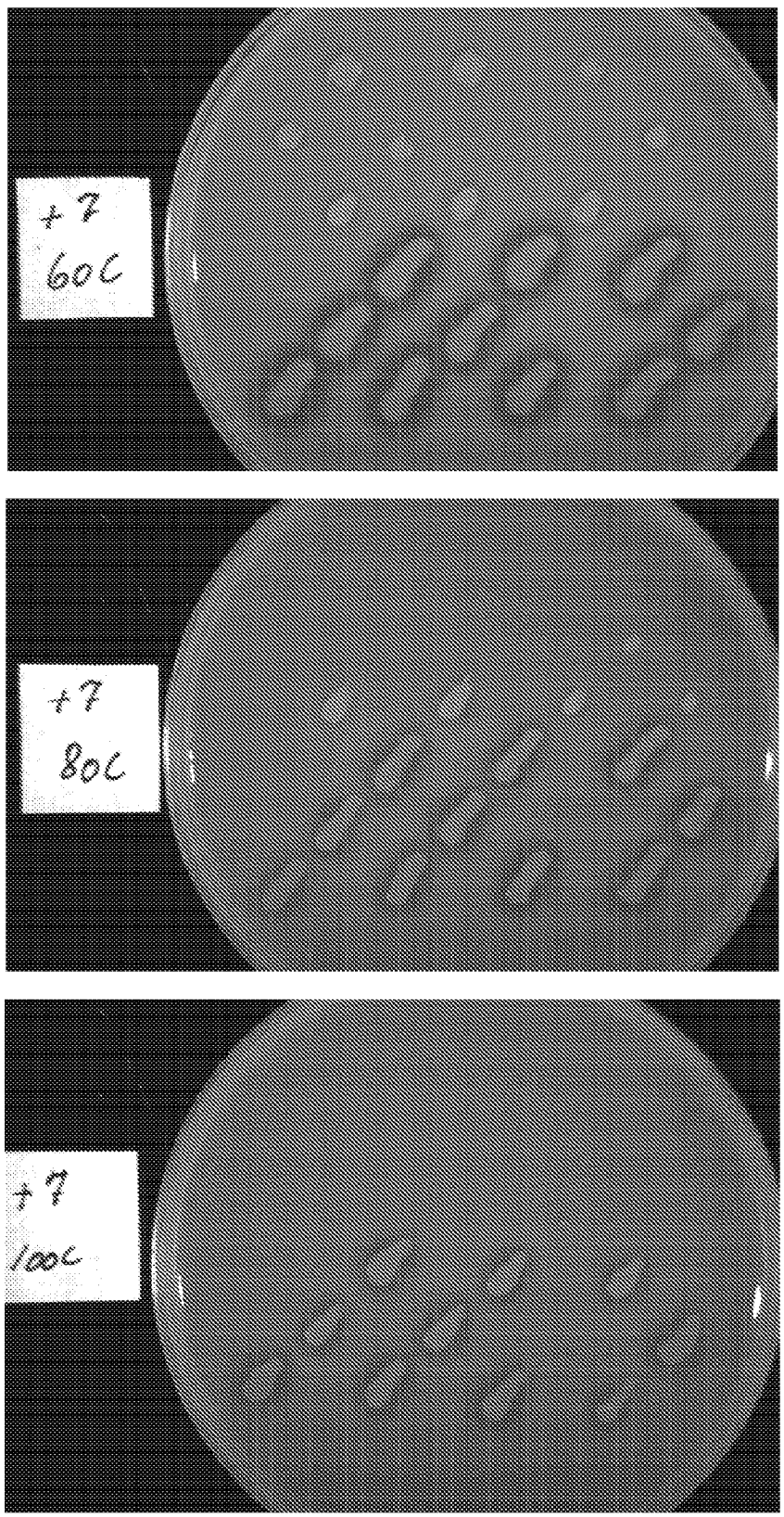
Figure 3A:
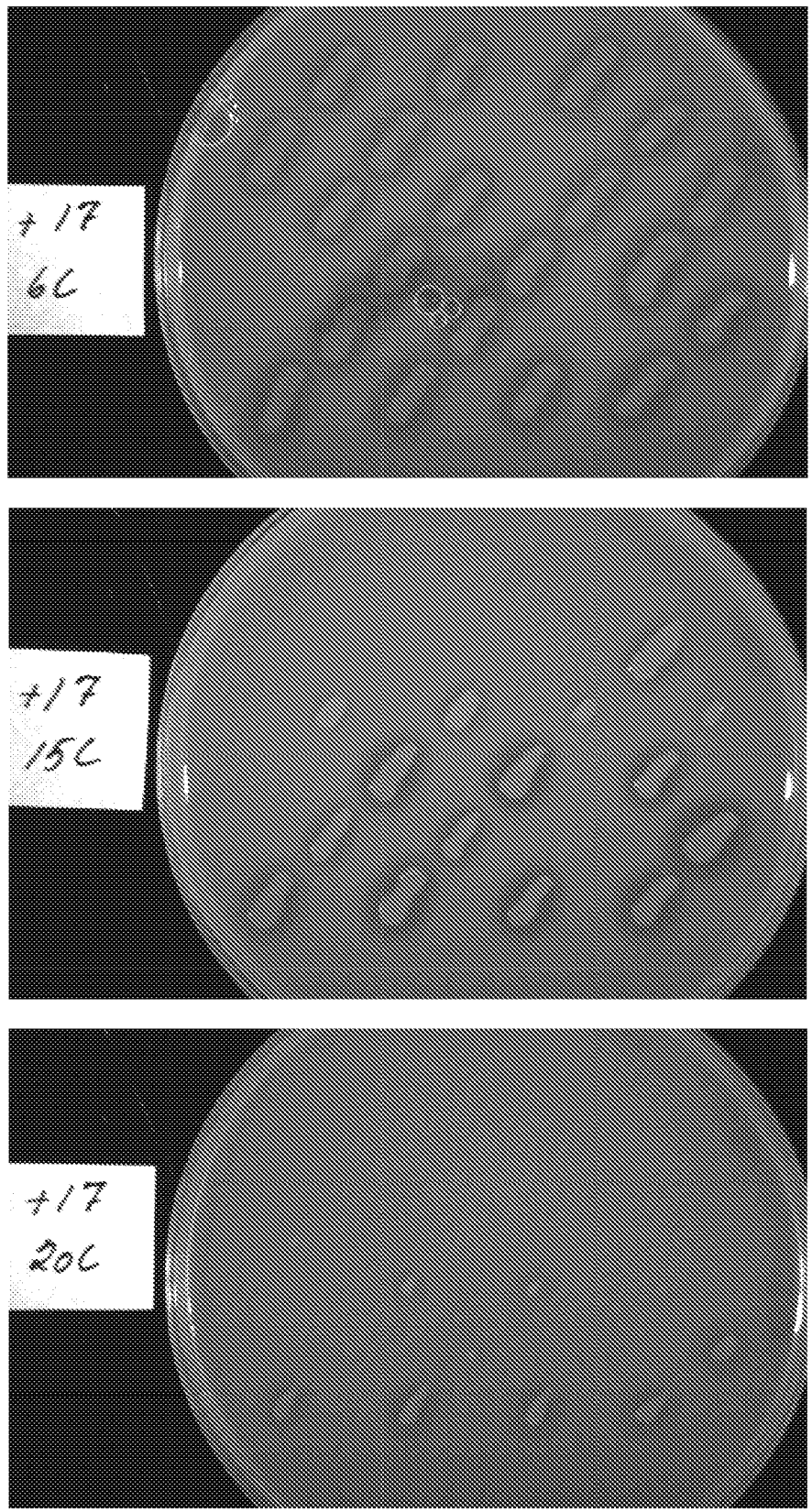
FIGS. 3A and 3B show testing of the 14 bp spacing constructs. The labelling is interpreted as follows: The "+17" indicates that it is the 14 bp spacing constructs. "6C" indicates that the plate contains 6 microgram/ml chloramphenicol, "15C" indicates it contains 15 microgram/ml chloramphenicol, etc., up to 35 microgram/ml chloramphenicol. We also tested on 40 microgram/ml but there was no growth (not shown).
Figure 3B:
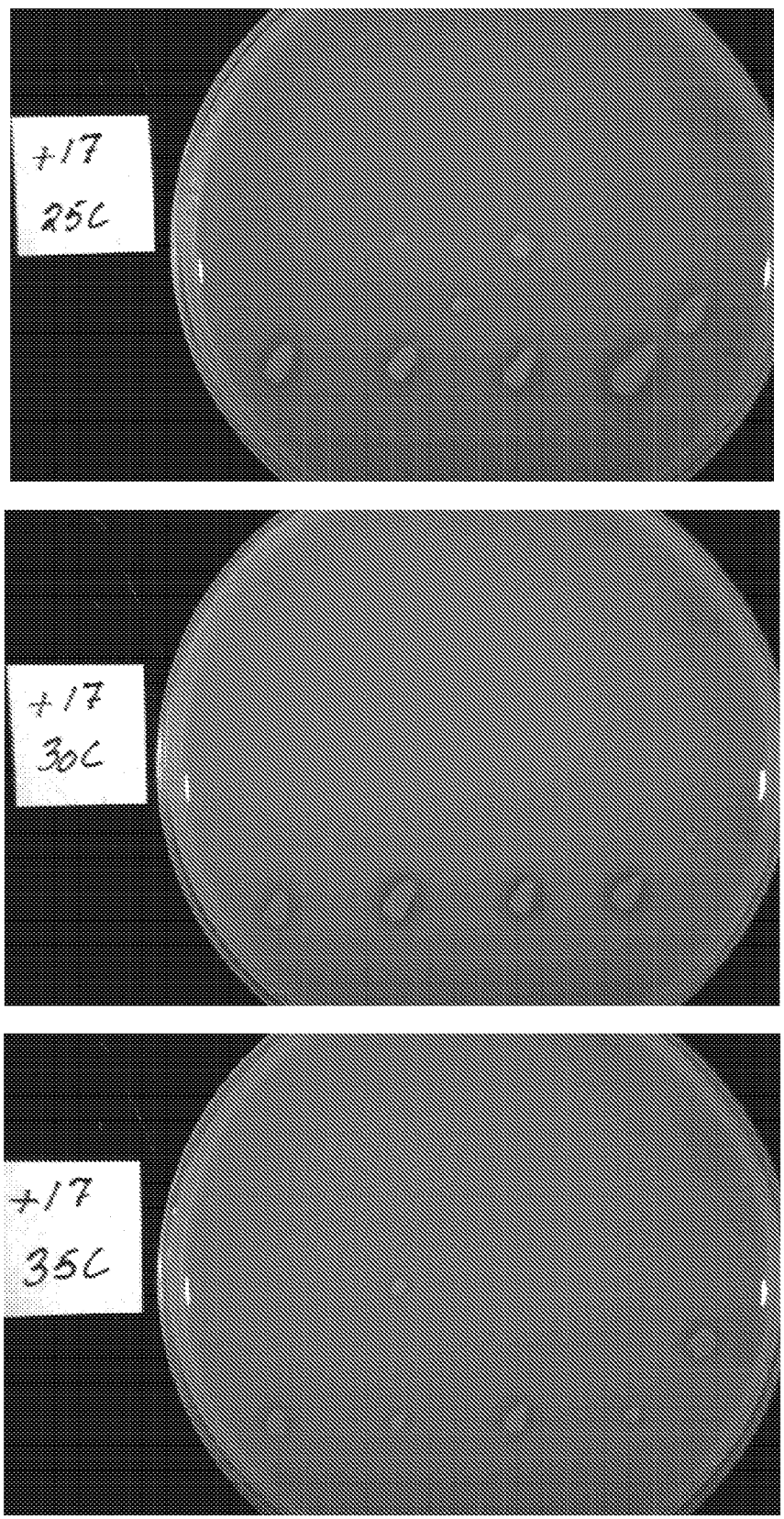

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct comprising a polynucleotide of the present invention, in particular a microbial host cell, either a eukaryotic or prokaryotic host cell.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

DETAILED DESCRIPTION OF THE INVENTION

The first aspect the invention relates to a method of indirectly identifying a polynucleotide comprising an open reading frame having an improved expression level from a library of polynucleotides encoding the same polypeptide of interest, or variants or homologues thereof, in a host cell expression library, the method comprising the steps of:

a) providing an expression library in a host cell, said library comprising at least two different open reading frames encoding the same polypeptide of interest, or variants or homologues thereof, each open reading frame being translationally coupled to a downstream gene encoding a screenable or selectable reporter;

b) culturing the host cell under conditions conducive to the expression of the polypeptide of interest, or variant or homologue thereof; and c) screening and/or selecting for a host cell having an improved expression level of the translationally coupled reporter when compared to one or more other host cells of the library, thus indirectly identifying a polynucleotide comprising an open reading frame having an improved expression level in the host cell.

The second aspect of the invention relates to an expression library comprising at least two different open reading frames encoding the same polypeptide of interest, or variants or homologues thereof, each encoding open reading frame being translationally coupled to a downstream gene encoding a screenable or selectable reporter. The expression library of the invention may be comprised in a nucleic acid construct or in an expression vector, preferably an integrative sort of construct or vector.

The method of the invention is particularly well-suited for screening a library of different open reading frames encoding the same polypeptide of interest. However, as indicated in the first aspect, it may also be suitable for screening a library of different polynucleotides or more specifically open reading frames encoding variants or homologues of a polypeptide of interest, or variants or homologues thereof, in particular variants that only differ in a single or a few amino acid positions, such as, in 2 or more, 3, 4, 5, 10 or more positions that may be altered as described elsewhere herein; the homologues are preferably at least 90% identical to the polypeptide of interest, more preferably at least 95% identical, and most preferably at least 97% identical to the polypeptide of interest, when aligned according to the directions provided herein.

Aspects of the present invention relates to different polypeptides encoding variants of the polypeptide of interest, preferably comprising a conservative substitution, deletion, and/or insertion of one or more amino acids. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309:59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochem. 30:10832-10837; U.S. Pat. No. 5,223,409; WO 92/06204), and region-directed mutagenesis (Derbyshire et al., 1986, Gene 46:145; Ner et al., 1988, DNA 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, or variants or homologues thereof, and can be applied to polypeptides of unknown structure.

The total number of amino acid substitutions, deletions and/or insertions of amino acids in the variants in the aspects of the invention is 10, preferably 9, more preferably 8, more preferably 7, more preferably at most 6, more preferably at most 5, more preferably 4, even more preferably 3, most preferably 2, and even most preferably 1.

The homology between two amino acid sequences is described by the parameter "identity". For purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of the present invention and a different amino acid sequence is calculated as the number of exact matches in an alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap. The length of a sequence is the number of amino acid residues in the sequence.

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), *Bacillus clausii* alkaline protease (aprH) and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), or *Bacillus subtilis* neutral protease (nprT). Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, xyl and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

A conditionally essential gene may function as a non-antibiotic selectable marker. Non-limiting examples of bacterial conditionally essential non-antibiotic selectable markers are the dal genes from *Bacillus subtilis*, *Bacillus licheniformis*, or other Bacilli, that are only essential when the bacterium is cultivated in the absence of D-alanine. Also the genes encoding enzymes involved in the turnover of UDP-galactose can function as conditionally essential markers in a cell when the cell is grown in the presence of galactose or grown in a medium which gives rise to the presence of galactose. Non-limiting examples of such genes are those from *B. subtilis* or *B. licheniformis* encoding UTP-dependent phosphorylase (EC 2.7.7.10), UDP-glucose-dependent uridylyltransferase (EC 2.7.7.12), or UDP-galactose epimerase (EC 5.1.3.2). Also a xylose isomerase gene such as xylA, of Bacilli can be used as selectable markers in cells grown in minimal medium with xylose as sole carbon source. The genes necessary for utilizing gluconate, gntK, and gntP can also be used as selectable markers in cells grown in minimal medium with gluconate as sole carbon source. Other examples of conditionally essential genes are known in the art. Antibiotic selectable markers confer antibiotic resistance to such antibiotics as ampicillin, kanamycin, chloramphenicol, erythromycin, tetracycline, neomycin, hygromycin or methotrexate.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s).

To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

The final aspect of the invention relates to a host cell comprising an expression library as defined in the second aspect.

In a preferred embodiment of the invention, the expression library comprises at least 2 different open reading frames encoding the same polypeptide of interest, or variants or homologues thereof; preferably at least 5; at least 10; at least 20; at least 50; 100; 500; 1,000; or most preferably at least 5,000 different open reading frames encoding the same polypeptide of interest, or variants or homologues thereof.

In preferred embodiments of the invention, the host cell is prokaryotic, and preferably Gram positive, preferably the Gram positive host cell is a *Bacillus* cell, preferably a *Bacillus* cell chosen from the group consisting of *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis*, *Streptococcus pyogenes*, *Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes*, *Streptomyces avermitilis*, *Streptomyces coelicolor*, *Streptomyces griseus*, and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, Molecular General Genetics 168: 111-115), by using competent cells (see, e.g., Young and Spizizen, 1961, Journal of Bacteriology 81: 823-829, or Dubnau and Davidoff-Abelson, 1971, Journal of Molecular Biology 56: 209-221), by electroporation (see, e.g., Shigekawa and Dower, 1988, Biotechniques 6: 742-751), or by conjugation (see, e.g., Koehler and Thorne, 1987, Journal of Bacteriology 169: 5271-5278).

The introduction of DNA into an *E coli* cell may, for instance, be effected by protoplast transformation (see, e.g., Hanahan, 1983, J. Mol. Biol. 166: 557-580) or electroporation (see, e.g., Dower et al., 1988, Nucleic Acids Res. 16: 6127-6145). The introduction of DNA into a *Streptomyces* cell may, for instance, be effected by protoplast transformation and electroporation (see, e.g., Gong et al., 2004, Folia Microbiol. (Praha) 49: 399-405), by conjugation (see, e.g., Mazodier et al., 1989, J. Bacteriol. 171: 3583-3585), or by transduction (see, e.g., Burke et al., 2001, Proc. Natl. Acad. Sci. USA 98: 6289-6294). The introduction of DNA into a *Pseudomonas* cell may, for instance, be effected by electroporation (see, e.g., Choi et al., 2006, J. Microbiol. Methods 64: 391-397) or by conjugation (see, e.g., Pinedo and Smets, 2005, Appl. Environ. Microbiol. 71: 51-57). The introduction of DNA into a *Streptococcus* cell may, for instance, be effected by natural competence (see, e.g., Perry and Kuramitsu, 1981, Infect. Immun. 32: 1295-1297), by protoplast transformation (see, e.g., Catt and Jollick, 1991, Microbios. 68: 189-2070, by electroporation (see, e.g., Buckley et al., 1999, Appl. Environ. Microbiol. 65: 3800-3804) or by conjugation (see, e.g., Clewell, 1981, Microbiol. Rev. 45: 409-436). However, any method known in the art for introducing DNA into a host cell can be used. The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori*, *Aspergillus fumigatus*, *Aspergillus foetidus*, *Aspergillus japonicus*, *Aspergillus nidulans*, *Aspergillus niger* or *Aspergillus oryzae* cell. In another most preferred aspect, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In another most preferred aspect, the filamentous fungal host cell is a *Bjerkandera adusta*, *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Coprinus cinereus*, *Coriolus hirsutus*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Tricho-*

*derma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, Proceedings of the National Academy of Sciences USA 81: 1470-1474. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source. The introduction of a vector into a bacterial host cell may, for instance, be effected by protoplast transformation (see, e.g., Chang and Cohen, 1979, Molecular General Genetics 168: 111-115), using competent cells (see, e.g., Young and Spizizin, 1961, Journal of Bacteriology 81: 823-829, or Dubnau and Davidoff-Abelson, 1971, Journal of Molecular Biology 56: 209-221), electroporation (see, e.g., Shigekawa and Dower, 1988, Biotechniques 6: 742-751), or conjugation (see, e.g., Koehler and Thorne, 1987, Journal of Bacteriology 169: 5771-5278).

Also, in preferred embodiments of the invention, the polypeptide of interest, or variants or homologues thereof, is an enzyme, preferably the enzyme is a lyase, a ligase, a hydrolase, an oxidoreductase, a transferase, or an isomerase, and more preferably the enzyme is an amylolytic enzyme, a lipolytic enzyme, a proteolytic enzyme, a cellulytic enzyme, an oxidoreductase or a plant cell-wall degrading enzyme, and more preferably an enzyme with an activity selected from the group consisting of aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinase, peroxidase, phytase, phenoloxidase, polyphenoloxidase, protease, ribonuclease, transferase, transglutaminase, or xylanase.

In preferred embodiments relating to the first and third aspects of the invention, the expression library is integrated into the genome of the host cell, preferably the expression library is site-specifically integrated into the same locus of each host cell in at least one copy.

In another preferred embodiment, the at least two different open reading frames in the expression library encoding the same polypeptide of interest, or variants or homologues thereof, are transcribed from at least one heterologous promoter, preferably the at least one heterologous promoter comprises an artificial promoter, more preferably the artificial promoter comprises one or more mRNA-stabilizing sequence, preferably derived from the cryIIIa promoter.

It is also preferred that the screenable or selectable reporter of the expression library is a cytosolic or cell-associated protein, preferably a fluorescent protein. Or in another embodiment, the screenable or selectable reporter of the expression library is a secreted protein.

Still another preferred embodiment relates to the expression library of the invention, wherein the screenable or selectable reporter provides an antibiotic resistance to the host cell.

Another preferred embodiment involves the construction of a reporter gene setup, in which an upstream open reading frame, encoding the protein of interest, or variants or homologues thereof, and provided in the form of a multitude of different, synthetic gene sequences encoding the same protein, or variants or homologues thereof, is linked by the mechanism of translational coupling to a downstream open reading frame encoding the reporter gene so that translation of the reporter gene is dependent upon translation of the gene encoding the protein of interest, but so that the two gene products are still produced as different polypeptides. The reporter gene may be a selectable marker gene, e.g. an antibiotic resistance encoding gene, or it may encode an easily screenable protein, e.g., a fluorescent protein. This setup has the particular advantage, that the protein of interest may be a secreted protein, whereas the reporter gene can encode a cytosolic, cell associated protein, which then allows the selection or isolation of a cell containing a well-translated version of the gene for the protein of interest, or variants or homologues thereof, based on that same cell's content of the cell-bound reporter protein.

It could be advantageous to also optimize the reporter gene prior to its use in the present invention to avoid expression bottlenecks or limitations for the screening/selection assay that might be caused by the reporter gene in itself, preferably the gene encoding a screenable or selectable reporter in the expression library of the invention is optimized for expression in said host cell, preferably by optimizing codon usage.

In a preferred embodiment of the invention, each open reading frame encoding the protein of interest, or variants or homologues thereof, in the expression library is translationally coupled to the downstream gene encoding the screenable or selectable reporter such that the start codon of the reporter gene is no more than 500 bp downstream of the stop-codon of the polypeptide encoding open reading frame, preferably no more than 400 bp, 300 bp, 200 bp, 100 bp, 50 bp, 25 bp, 10 bp, 5 bp, or 1 bp downstream of the stop-codon of the polypeptide encoding open reading frame; preferably each open reading frame encoding the protein of interest, or variants or homologues thereof, is translationally coupled to the downstream gene encoding the screenable or selectable reporter such that the start codon of the reporter gene overlaps with the stop-codon of the polypeptide encoding open reading frame, preferably as follows: A<u>TGA</u>, wherein the stop-codon is underscored and the start-codon is bold.

EXAMPLES

LB agar, TY bouillon medium and BPX shake flask medium have all been described in Patent Publication WO 94/14968.

PS-1 shake flask medium (10% sucrose, 4% soybean flour, 1% Na2SO4.12H20, 0.5% CaCO3, and 0.01% pluronic acid) has been described in U.S. Pat. No. 6,255,076, example 28.

The strains can be evaluated by shake flask fermentation, by inoculation into PS-1 medium and incubation at 30° C. for 5 days, at 300 rpm, and the protease activity of full culture samples can be determined, using the PNA assay with succinyl-alanine-alanine-proline-phenylalnine-paranitroanilide as a substrate. The principle of the PNA assay is described in Rothgeb, T. M., Goodlander, B. D., Garrison, P. H., and Smith, L. A., Journal of the American Oil Chemists' Society, Vol. 65 (5) pp. 806-810 (1988).

Example 1

This example shows the construction of different synthetic genes encoding the same secreted polypeptide. However, expression of the two genes in Bacillus licheniformis results in significantly different yields.

One example of a synthetic gene, encoding a protease polypeptide (10R) originally produced by a bacterial strain of the genus Nocardiopsis, is the gene contained on plasmid pSJ6074, described in WO 2005/123915, example 3. This particular synthetic gene will in the following be named 10R_pSJ6074.

This gene was transferred to an integration vector designed to allow integration of the protease expression cassette into the chromosome of a B. licheniformis strain, that already contains a synthetic triple promoter (WO 1999/043835) integrated at the amyL locus, by double homologous recombination at the cryIIIA stabilizer and downstream amyL segments. Further description of suitable host strains and integration procedures are found in WO 2005/123915.

The final integration vector, pSJ6094, was constructed by excision of the 1.8 kb EcoRI-HindIII fragment from pSJ6074, and ligation of this fragment to the 4.6 kb EcoRI-HindIII fragment of pSJ5487 (described in WO 2005/123915, example 3). The ligation mixture was transformed into B. subtilis PL1801 competent cells, selecting erythromycin resistance (2 microgram/ml) at 30° C. B. subtilis PL1801 is a derivative of B. subtilis DN1885 (Diderichsen et al., 1990, J. Bacteriol. 172(8): 4315-4321) with deletions in the protease genes apr and npr. A resulting transformant was SJ6094 (PL1801/pSJ6094).

A slightly different synthetic gene, encoding the same polypeptide product as above, is present on the integration vector plasmid pSJ7802 which was constructed as follows:

Plasmid pSJ6074 was used as template in a PCR amplification with primers:

```
PEP1 (SEQ ID NO: 1):
5'-TATCTTGAAAGGAGGGATGCC

#431991 (SEQ ID NO: 2):
5'-GACTACGCGTTATGTTCTAAGTCTTACTCCCCAAGAATTGACCA
TCGGAGTGACTTCTTGGTAGAACGTTGTGCCACCTG
```

The PCR amplified fragment was digested with BsiWI and MluI and the 170 bp fragment was ligated to the 6.3 kb MluI-BsiWI fragment from pSJ6094. The ligation mixture was transformed into PL1801 competent cells, as above. A resulting transformant was SJ7802 (PL1801/pSJ7802). This particular synthetic gene will in the following be named 10R_pSJ7802.

The two synthetic protease genes only differ within the last approximately 50 basepairs of the coding regions.

B. licheniformis host strain TH6 has been described in WO 2005/123915, example 6.

Both integration vectors pSJ6094 and pSJ7802 were transferred individually to strain TH6 and their protease expression cassettes were integrated into the chromosome, essentially as described in WO 2005/123915. The protease yields from the resulting strains, which harboured either one or the other synthetic protease gene expressed from one chromosomal copy with exact identical expression control regions, were compared in shake flask fermentations (PS1 medium, incubated for 5 days at 30° C.).

This revealed that the average protease yield from flasks with strains containing the 10R_pSJ7802 gene was 7.6 times higher than the yield from flasks from a strain containing 10R_pSJ6074.

This is an example of a yield difference between two, apparently very similar, synthetic gene sequences, where it would be desirable to have a quick screening/selection method that enabled an identification and/or selection of the strain containing the high-yielding gene from strains containing the low-yielding gene.

Example 2

Construction of a Translationally Coupled Selection Construct for Synthetic 10R Genes Selection of well-translated 10R synthetic gene sequences by translational coupling to the pC194-derived cat gene is performed using constructs in which the 10R stop codon is TGA, and the cat start codon is an upstream overlapping ATG, as shown in the following: ATGA, wherein the 10R stop codon is underscored and the cat start codon is bold.

The selection construct may be put together essentially as described for the construct contained in strain PL3598-37 (WO 03/095658, example 1), with the important difference that the BPN' open reading frame is replaced by the translationally coupled 10R+cat open reading frames.

The construct, useful for direct transformation into the Bacillus subtilis chromosome to create a selectable population of cells, comprises the following elements:

An upstream region for homologous integration, consisting of sequences from the B. subtilis pectate lyase chromosomal region (pel_upstream);

A spectinomycin resistance gene (spc) flanked by resolvase recognition sites (res);

A synthetic promoter region including the cryIIIA mRNA stabilizing leader sequence (Ptriple+cryIIIA_stab, WO 1999/043835);

A 10R synthetic gene sequence, translationally coupled to the cat gene from pC194; and A downstream region for homologous integration, consisting of sequences from the B. subtilis pectate lyase chromosomal region (pel_downstream).

It is to be understood that for creation of a library suitable for selection, a multitude of different synthetic 10R gene sequences is employed in the construction step, so that transformation of B. subtilis with the final DNA construct(s) results in the creation of a population of cells, each containing one particular synthetic 10R gene sequence.

Chromosomal DNA from strain PP1617 (also named PL3598-37, WO 03/095658, example 1) was extracted and used as template in PCR reactions with the following primer combinations:

A) Amplification of a fragment containing the upstream region for homologous recombination (pel_upstream), together with the res-spc-res segment was done using the following primers, and an annealing temperature of 65° C.:

Downstream reading primer, #519841:

```
                                              (SEQ ID NO: 3)
        NheI    SphI
5'-GAGCTAGCGCATGCGTCTCACTTCCTTACTGCGTCTGG
```

Upstream reading primer, #519842:

```
       KpnI    XbaI  BglII
5'-TGCGGTACCTGATCTAGATCTCGGG    (SEQ ID NO: 4)
```

The amplified fragment was cloned into a suitable cloning vector from which it could be excised using SphI and XbaI, for propagation and preparation of large quantities of DNA. This was done by digestion of the fragment with SphI and KpnI, gel purification of the 4.4 kb fragment, and ligation of this to plasmid vector pUC19 which had been digested with SphI and KpnI. The ligation mixture was transformed, by electroporation, into *E. coli* SJ2 (Diderichsen et al., 1990, J. Bacteriol. 172(8): 4315-4321) selecting ampicillin resistance, and a transformant (which also exhibited spectinomycin resistance) was kept as SJ8729 (SJ2/pSJ8729).

Alternatively, the fragment can be used as directly prepared by the PCR amplification, and digested with SphI and XbaI.

B) Amplification of a fragment, containing the triple promoter region (Ptriple) was done using the following primers, and an annealing temperature of 65° C.:

Downstream reading primer, #519843:

```
    BglII XbaI
5'- CGAGATCTAGATCAGGTACCGCAAC    (SEQ ID NO: 5)
```

Upstream reading primer, #519844:

```
                                              (SEQ ID NO: 6)
     EcoRI
5'- GACTGAATTCAATTAAGCTTAACATTAATAATTCTTCAATTGC
```

This fragment was cloned into a suitable cloning vector from which it could be excised using XbaII and EcoRI, for propagation and preparation of large quantities of DNA. This was done by digestion of the amplified fragment with EcoRI and BglII, gel purification of the 0.4 kb fragment, and ligation of this to the 5.1 kb EcoRI-BglII fragment of pSJ2739 (U.S. Pat. No. 6,100,063). The ligation mixture was transformed into *B. subtilis* DN1885 competent cells, selecting erythromycin resistance (2 microgram/ml) at 30° C. Two transformants were kept as SJ8722 (DN1885/pSJ8722) and SJ8723 (DN1885/pSJ8723).

Alternatively, the fragment may be used as directly prepared by the PCR amplification, and digested with XbaI and EcoRI.

C) Amplification of a fragment containing the downstream region for homologous recombination (pel_downstream) was done using the following primers, and an annealing temperature of 65° C.:

Downstream reading primer, #519845:

```
                                            (SEQ ID NO: 7)
      BamHI
5'- GACTGGATCCGGTTCGCGTCCGGACAGCACATC
```

Upstream reading primer, #519846:

```
                                            (SEQ ID NO: 8)
     SphI EagI,NotI
5'- GACTGCATGCGGCCGCTTTTTCACCACAGCACCAGCC
```

This fragment was cloned into a suitable cloning vector from which it could be excised using BamHI and EagI, for propagation and preparation of large quantities of DNA. This was done by digestion of the amplified fragment with BamHI and SphI, gel purification of the 2.3 kb fragment, and ligation of this to pUC19, which had been digested with BamHI and SphI. The ligation mixture was transformed, by electroporation, into *E. coli* SJ2 selecting ampicillin resistance, and transformants kept as SJ8724 (SJ2/pSJ8724) and SJ8725 (SJ2/pSJ8725). Both of these plasmids harboured mutations, introduced during PCR amplification, but a plasmid containing a fragment useful for integration was constructed by ligation of the 0.4 kb NsiI-BseRI fragment from pSJ8724 to the 4.6 kb BseRI-NsiI fragment from pSJ8725. Two resulting transformants of *E. coli* SJ2 were kept as SJ8732 (SJ2/pSJ8732) and SJ8733 (SJ2/pSJ8733).

Alternatively, the fragment may be used as directly prepared by the PCR amplification, and digested with BamHI and EagI.

D) The cat gene, originally from pC194, was amplified from plasmid pDN1050 (Diderichsen et al., 1993, Plasmid 30, 312-315) using the following primers and an annealing temperature of 65° C.:

Primer cat gene, #519849 (SOE primer, starting at start codon, common for all constructs; positions 1127-1095 in pDN1050):

```
                                          (SEQ ID NO: 9)
5'-ATGAACTTTAATAAAATTGATTTAGACAATTGG
```

Upstream cat reading primer, #519848 (downstream stop codon of cat gene; positions 478-505 in pDN1050):

```
                                              (SEQ ID NO: 10)
      HindIII MluI
5'-GACTAAGCTTACGCGTTATAAAAGCCAGTCATTAGGCCTATCTG
```

E) Plasmid pSJ6074 (see example 1) was used as cloning vector for construction of the translationally coupled synthetic 10R and cat genes. A 10R_pSJ6074 gene segment was amplified from pSJ6074 using the following primers and an annealing temperature of 65° C.:

Downstream reading primer #519847, upstream BamHI site (pos. 1907-1931 in pSJ6074):

```
5'-AGCGTGAGCTATCCTGAAGGTACCG    (SEQ ID NO: 11)
```

Upstream 10R_pSJ6074 gene SOE primer #519850 (pos. 2112-2089 in pSJ6074):

```
                                                   (SEQ ID NO: 12)
5'-CCAATTGTCTAAATCAATTTTATTAAAGTTCATGTACGGAGTCTAAC
TCCCCAAGAG
<-- complementary to SEQ ID NO: 9) --><-- pSJ6074
2112-2089-->
```

F) A 10R_pSJ7802 gene segment was amplified from pSJ7802 (see example 1) using the following primers and an annealing temperature of 65° C.:

Downstream reading primer #519847, upstream BamHI site (pos. 1907-1931 in pSJ6074), the same primer as used for the 10R_pSJ6074 gene:

```
5'-AGCGTGAGCTATCCTGAAGGTACCG    (SEQ ID NO: 11)
```

Upstream 10R_pSJ7802 gene SOE primer #519851 (pos. 1716-1690 in pSJ7802):

```
                                                    (SEQ ID NO: 13)
5'-CCAATTGTCTAAATCAATTTTATTAAAGTTCATGTTCTAAGTCTTAC
TCCCCAAGAATTG
<- complementary to SEQ ID NO: 9) -><- pSJ7802
1716-1690->
```

A 10R_pSJ6074 gene cat gene translationally coupled construct was prepared by assembling, in a SOE PCR reaction, the cat gene fragment amplified from pDN1050 DNA using primers (SEQ ID NO: 9) and (SEQ ID NO: 10), above, with the 10R_pSJ6074 gene segment amplified from pSJ6074 DNA using primers (SEQ ID NO: 11) and (SEQ ID NO: 12), above, using primers (SEQ ID NO: 11) and (SEQ ID NO: 10) and an annealing temperature of 65° C. for amplification of the final SOE construct. This final SOE construct was then digested with BamHI and HindIII, the 0.75 kb fragment gel purified, and ligated to BamHI+HindIII digested pUC19. The ligation mixture was transformed by electroporation into E. coli SJ2, selecting ampicillin resistance, and two transformants kept as SJ8726 (SJ2/pSJ8726) and SJ8727 (SJ2/pSJ8727). The 0.75 kb insert in pSJ8726 was subsequently excised using BamHI and MluI, and ligated to the 4.35 kb MluI-BamHI fragment of pSJ6074, thus replacing the 3' end of the 10R_pSJ6074 gene in pSJ6074 with the 3' end translationally coupled to the cat gene. The ligation mixture was transformed into E. coli SJ388 (a dam– strain), and two transformants kept as SJ8758 (SJ388/pSJ8758) and SJ8759 (SJ388/pSJ8759).

A 10R_pSJ7802 gene-cat gene translationally coupled construct was prepared by assembling, in a SOE PCR reaction, the cat gene fragment amplified from pDN1050 DNA using primers (SEQ ID NO: 9) and (SEQ ID NO: 10), above, with the 10R_pSJ7802 gene segment amplified from pSJ7802 DNA using primers (SEQ ID NO: 11) and (SEQ ID NO: 13), above, using primers (SEQ ID NO: 11) and (SEQ ID NO: 10) and an annealing temperature of 65° C. for amplification of the final SOE construct. This final SOE construct was then digested with BamHI and HindIII, the 0.75 kb fragment gel purified, and ligated to BamHI+HindIII digested pUC19. The ligation mixture was transformed by electroporation into E. coli SJ2, selecting ampicillin resistance, and a transformant kept as SJ8728 (SJ2/pSJ8728). The 0.75 kb insert in pSJ8728 was subsequently excised using BamHI and MluI, and ligated to the 4.35 kb MluI-BamHI fragment of pSJ6074, thus replacing the 3' end of the 10R_pSJ6074 gene in pSJ6074 with the corresponding segment from the 10R_pSJ7802 gene translationally coupled to the cat gene. The ligation mixture was transformed into E. coli SJ388 (a dam– strain), and two transformants kept as SJ8786 (SJ388/pSJ8786) and SJ8787 (SJ388/pSJ8787).

The different versions of 10R genes translationally coupled to the cat gene are excised from the pSJ6074-based plasmids (pSJ8758, pSJ8759 and pSJ8786, pSJ8787, respectively) as EcoRI-BclI fragments, containing the cryIIIA_stab segment, the synthetic 10R gene sequence, and the cat gene.

The final DNA construct used for transformation of the B. subtilis competent host strain is then prepared by ligation of the following four fragments:

The SphI-XbaI fragment prepared under A), above, containing "pel_upstream+res-spc-res".

The XbaI-EcoRI fragment prepared under B), above, containing "Ptriple".

The EcoRI-BclI fragment(s) prepared under D), above, containing "cryIIIA_stab-10R synthetic gene-cat".

The BamHI-EagI fragment prepared under C), above, containing "pel_downstream".

The final construct(s) are prepared in large quantities by PCR amplification using primers 1) and 6), and the resulting PCR amplified fragment is transformed into competent B. subtilis cells as described in WO 03/095658.

It will be apparent to anyone skilled in the art, that alternative methods for construction of the final DNA construct to be used for transformation exist. One alternative is to avoid digestions and ligations, and to assemble the entire construct by SOE PCR, maybe requiring some modification of the primers used.

Another option, that appears to become increasingly appealing also from an economic point of view, is the total in-vitro synthesis of the entire construct. The desired variation in the region coding for the protein of interest can then be provided as an integrated feature in the total construct.

In accordance with the present invention, the above constructed B. subtilis strains containing either 10R_pSJ6074 translationally coupled to the cat gene, or 10R_pSJ7802 translationally coupled to the cat gene, are propagated and it is determined how the difference in the observed production level of 10R protease is reflected in differences in chloramphenicol resistance exhibited by the strains.

It is evident, that an increased chloramphenicol resistance for these strains can be used as a strong tool to select for a strain, wherein the synthetic 10R genes are well-expressed, since the chloramphenicol resistance phenotype of the strains is directly correlated with how well the 10R and cat genes are translated.

Example 3

This example illustrates the construction of and selection on a library of synthetic 10R gene sequences. In this particular case variation is introduced within the last 50 bp of the 10R coding sequence.

The following degenerate primer is designed for making the intended variation:

```
                                                      (SEQ ID NO:14)
5'-CCAATTGTCTAAATCAATTTTATTAAAGTTCATGTNCGNAGNCGNACNCCCCANGARTT-
              <- complementary to ID NO:9 ) ->

-NACCATNGGNGTNACYTCYTGGTAGAACGTTGTGCCACCTG
                          <- pSJ6074 pos.2067-2046
``` wherein the symbols have the following meaning:

| Symbol | Meaning |
| --- | --- |
| a | a; adenine |
| c | c; cytosine |
| g | g; guanine |
| t | t; thymine in DNA; uracil in RNA |
| m | a or c |
| r | a or g |
| w | a or t |
| s | c or g |
| y | c or t |
| k | g or t |

-continued

| Symbol | Meaning |
|---|---|
| v | a or c or g; not t |
| h | a or c or t; not g |
| d | a or g or t; not c |
| b | c or g or t; not a |
| n | a or c or g or t |

Plasmid pSJ6074 is used as template in a PCR amplification with the following primers:

Downstream reading primer, upstream BamHI site (pos. 1907-1931 in pSJ6074):

```
5'-AGCGTGAGCTATCCTGAAGGTACCG      (SEQ ID NO: 11)
``` and the above primer SEQ ID NO:14.

A library of different synthetic 10R genes each translationally coupled to the cat gene is prepared by assembling, in a SOE PCR reaction, the cat gene fragment amplified using primers (SEQ ID NO: 9) and (SEQ ID NO: 10), as described in example 2 above, with the 10R gene segment amplified using primers (SEQ ID NO: 11) and (SEQ ID NO: 14), above, using primers (SEQ ID NO: 11) and (SEQ ID NO: 10) for amplification of the final SOE construct. This final SOE construct is then digested with BamHI and MluI, and the BamHI-MluI fragment containing part of the 10R gene (with variation) and all of the cat gene open reading frame is inserted between BamHI and MluI in pSJ6074, thus replacing the 3' end of the 10R_pSJ6074 gene in pSJ6074 with the 3' end translationally coupled to the cat gene, and consisting of a number of different, synthetic sequences.

The result is a pool of pSJ6074-like plasmids, each having its own, particular sequence of the 10R gene, which are used in a construction according to the procedure given in example 2. The final DNA construct (still encompassing a number of different, synthetic 10R sequences) is then transformed into competent *B. subtilis* cells, and the resulting transformants are propagated, either in liquid medium or on agar plates, and subjected to chloramphenicol resistance selection in order to identify those transformants exhibiting the highest degrees of chloramphenicol resistance. Resulting, selected transformants are subsequently assayed for their 10R production ability.

Example 4

Construction of a Translationally Coupled Selection Construct for Synthetic 10R Genes with a Spacing of 4 bp As a test of the selection principle, a construct was designed in which a synthetic 10R gene sequence, that in *B. licheniformis* resulted in a low protease 10R yield, was translationally coupled to the pC194-derived cat gene, and compared to a construct in which a different synthetic 10R gene sequence, that in *B. licheniformis* resulted in a high protease 10R yield, was translationally coupled to the pC194-derived cat gene.

The translational coupling setup was in both cases such that the stop codon for the synthetic 10R gene (TAA) was followed by a 4 bp region (CGCG), which again was followed by the start codon for the cat gene (ATG).

*Bacillus subtilis* strains containing the low-yielding gene, 10R_pSJ6074, were SJ8919 and SJ8920, and *Bacillus subtilis* strains containing the high-yielding gene, 10R_pSJ7802, were SJ8984 and SJ8985, constructed as described below.

4A) Construction of a 10R_pSJ6074-cat Translationally Coupled Construct.

Several DNA fragments used in the strain constructions were prepared as described in Example 2, sections A), B), C), and D). In addition, the following fragment was used for the low yielding gene:

Plasmid pSJ6074 (see example 1) was used as cloning vector for construction of the translationally coupled synthetic 10R and cat genes. A 10R_pSJ6074 gene segment was amplified from pSJ6074 using the following primers and an annealing temperature of 65° C.:

Downstream reading primer #519847, upstream BamHI site (pos. 1907-1931 in pSJ6074)

```
(SEQ ID NO: 11):    5'-AGCGTGAGCTATCCTGAAGGTACCG
```

Upstream 10R_pSJ6074 gene SOE primer #535797 (pos. 2120-2096 in pSJ6074):

```
(SEQ ID NO: 15):
5'-CCAATTGTCTAAATCAATTTTATTAAAGTTCAtcgcgttaTGTACGG

AGTCTAACTCC
<-complementary to SEQ ID NO: 9) -><-
pSJ6074 2120-2096 ->
```

A 10R_pSJ6074 gene-cat gene translationally coupled construct was prepared by assembling, in a SOE PCR reaction, the cat gene fragment amplified from pDN1050 DNA using primers (SEQ ID NO: 9) and (SEQ ID NO: 10), (Example 2, D)), with the 10R_pSJ6074 gene segment amplified from pSJ6074 DNA using primers (SEQ ID NO: 11) and (SEQ ID NO: 15), above, using primers (SEQ ID NO: 11) and (SEQ ID NO: 10) and an annealing temperature of 65° C. for amplification of the final SOE construct. This final SOE construct was then digested with BamHI+MluI, and the 0.75 kb fragment was ligated to the 4.35 kb MluI-BamHI fragment of pSJ6074, thus replacing the 3' end of the 10R_pSJ6074 gene in pSJ6074 with the 3' end translationally coupled to the cat gene.

The ligation mixture was transformed into *E. coli* SJ2, and a transformant having the correct DNA sequence of the PCR amplified insert was kept as SJ8846 (SJ2/pSJ8846). Plasmid pSJ8846 was transformed into *E. coli* SJ388 (a dam– strain), and two transformants kept as SJ8861 (SJ388/pSJ8846) and SJ8862 (SJ388/pSJ8846).

Finally, a 2.5 kb EcoRI-BclI fragment containing the cryIIIA_stab segment, the 10R_pSJ6074 gene sequence, and the cat gene, was excised and purified from pSJ8846 extracted from the dam– host.

The final DNA construct used for transformation of *B. subtilis* was prepared by ligation of the following four fragments:

A SphI-BglII fragment prepared as described in Example 2, A), containing "pel_upstream+res-spc-res". The fragment (4.4 kb) was excised from pSJ8729 and gel purified.

A BglII-EcoRI fragment prepared as described in Example 2, B), containing "Ptriple". The fragment (0.44 kb) was excised from pSJ8722 and gel purified.

The EcoRI-BclI fragment prepared as described under 4A), above, containing "cryIIIA_stab-10R synthetic gene-cat". The fragment (2.5 kb) was excised from pSJ8846 and gel purified.

A BamHI-SphI fragment prepared as described in Example 2, C), containing "pel_downstream". The fragment (2.3 kb) was excised from pSJ8724 and gel purified.

Initially, the 2.5 kb EcoRI-BclI fragment and the 2.3 kb BamHI-SphI fragment were mixed and ligated, the ligation mixture was then digested with EcoRI and SphI, the enzymes heat inactivated, the 4.4 kb SphI-BglII fragment and the 0.44 kb BglII-EcoRI fragment were added and the mixture ligated again, and this ligation mixture was subsequently used to transform competent cells of *B. subtilis* PL1801 to spectinomycin resistance (180 microgram/ml). By replica plating, more than 50% of the colonies appearing on the spectinomycin plates were found to be chloramphenicol resistant (to 6 microgram/ml), and to be protease positive on plates with skim milk. 2 such strains were kept as SJ8919 and SJ8920.

4B) Construction of a 10R_pSJ7802-cat Translationally Coupled Construct.

Several DNA fragments used in the strain constructions were prepared as described in Example 2, sections A), B), C), and D). In addition, the following fragments were used for the high yielding gene:

Plasmid pSJ8847 was used as cloning vector for construction of the translationally coupled synthetic 10R_pSJ7802 and cat genes. Plasmid pSJ8847 is very similar to pSJ8846, described above, the only difference being that the following, slightly different upstream reading 10R SOE primer was used in its construction:

Upstream 10R_pSJ6074 gene SOE primer #535798 (pos. 2124-2097 in pSJ6074)

```
(SEQ ID NO: 16):
5'-CCAATTGTCTAAATCAATTTTATTAAAGTTCAtagcacgcgttaTGT

ACGGAGTCTAACTC
<-complementary to SEQ ID NO: 9) -><-
pSJ6074 2124-2097 ->
```

A 10R_pSJ7802 gene segment was amplified from pSJ7802 using the following primers and an annealing temperature of 65° C.:

Downstream reading primer #289358, near start of synthetic 10R genes (pos. 659-679 in pSJ7802) (SEQ ID NO: 17):

```
(SEQ ID NO: 17):
5'-GACTAAGCTTCTGCAGCAGCGGCGGCTACTGGAGCATTACCTCAG
                            <- pSJ7802 659-679 ->
```

Upstream 10R_pSJ7802 gene SOE primer #542633 (pos. 1724-1700 in pSJ7802)

```
(SEQ ID NO: 18):
5'-CCAATTGTCTAAATCAATTTTATTAAAGTTCAtcgcgttaTGTTCTA

AGTCTTACTCC
<-complementary to SEQ ID NO: 9) -><-
pSJ7802 1724-1700 ->
```

The PCR amplified fragment was digested with MfeI+BamHI, and the 0.12 kb fragment gel purified. It was ligated to pSJ8847, which had been digested with MfeI+BamHI, and subsequently treated with alkaline phosphatase. The ligation mixture was transformed into *E. coli* SJ388, and two transformants, having the correct DNA sequence of the PCR amplified segment, were kept as SJ8964 (SJ388/pSJ8964) and SJ8965 (SJ388/pSJ8965).

As it was found difficult to obtain good quality plasmid DNA from SJ8729, it was decided to transfer the "pel_upstream+res-spc-res" fragment to a *B. subtilis* vector plasmid. The pUB110-derived vector plasmid pDN1050 was digested with SphI+BglII, and the 1.7 kb fragment gel purified. It was ligated to the gel purified 4.4 kb SphI-BglII fragment from pSJ8729, and the ligation mixture transformed into *B. subtilis* PL1801 selecting spectinomycin resistance (180 microgram/ml). Two transformants were kept as SJ8881 (PL1801/pSJ8881) and pSJ8882 (PL1801/pSJ8882).

The final translationally coupled DNA construct used for transformation of *B. subtilis* was prepared by ligation of the following four fragments:

A SphI-BglII fragment containing "pel_upstream+res-spc-res". The fragment (4.4 kb) was excised from pSJ8881 and gel purified.

A BglII-EcoRI fragment prepared as described in Example 2, B), containing "Ptriple". The fragment (0.44 kb) was excised from pSJ8722 and gel purified.

The EcoRI-BclI fragment prepared as described under 4B), above, containing "cryIIIA_stab-10R synthetic gene-cat". The fragment (2.5 kb) was excised from pSJ8964 and gel purified.

A BamHI-SphI fragment prepared as described in Example 2, C), containing "pel_downstream". The fragment (2.3 kb) was excised from pSJ8724 and gel purified.

Initially, the 2.5 kb EcoRI-BclI fragment and the 2.3 kb BamHI-SphI fragment were mixed and ligated, the ligation mixture was then digested with EcoRI and SphI, and the 4.8 kb fragment gel purified. The 4.4 kb SphI-BglII fragment and the 0.44 kb BglII-EcoRI fragment were added and the mixture ligated, and this ligation mixture was subsequently used to transform competent cells of *B. subtilis* PL1801 to spectinomycin resistance (180 microgram/ml). By replica plating, more than 50% of the colonies appearing on the spectinomycin plates were found to be chloramphenicol resistant (to 6 microgram/ml), to be protease positive on plates with skim milk, and to be devoid of pectate lyase activity, by a plate assay, confirming that they were obtained by a double homologous recombination event. 2 such strains were kept as SJ8984 and SJ8985.

Example 5

Construction of a Translationally Coupled Selection Construct for Synthetic 10R Genes with a Spacing of 14 bp As another test of the selection principle, a construct was designed in which a synthetic 10R gene sequence, that in *B. licheniformis* resulted in a low protease 10R yield, was translationally coupled to the pC194-derived cat gene, and compared to a construct in which a different synthetic 10R gene sequence, that in *B. licheniformis* resulted in a high protease 10R yield, was translationally coupled to the pC194-derived cat gene.

The translational coupling setup was in both cases such that the stop codon for the synthetic 10R gene (TAA) was followed by a 14 bp region (CGCGTGCTAGCGGC; SEQ ID NO:19) which again was followed by the start codon for the cat gene (ATG).

*Bacillus subtilis* strains containing the low-yielding gene, 10R_pSJ6074, were SJ8923 and SJ8924, and *Bacillus subtilis* strains containing the high-yielding gene, 10R_pSJ7802, were SJ8986 and SJ8987, constructed as described below.

5A) Construction of a 10R_pSJ6074-cat Translationally Coupled Construct.

Several DNA fragments used in the strain constructions were prepared as described in Example 2, sections A), B), C), and D). In addition, the following fragment was used for the low yielding gene:

Plasmid pSJ6074 (see example 1) was used as cloning vector for construction of the translationally coupled synthetic 10R and cat genes. A 10R_pSJ6074 gene segment was amplified from pSJ6074 using the following primers and an annealing temperature of 65° C.:

Downstream reading primer #519847, upstream BamHI site (pos. 1907-1931 in pSJ6074)

```
(SEQ ID NO: 11):    5'-AGCGTGAGCTATCCTGAAGGTACCG
```

Upstream 10R_pSJ6074 gene SOE primer #535799 (pos. 2130-2107 in pSJ6074)

```
(SEQ ID NO: 20):
5'-CCAATTGTCTAAATCAATTTTATTAAAGTTCAtgccgctagcacgcg ttaTGTACGG
<-complementary to SEQ ID NO: 9) -><-
pSJ6074 2130-2107 ->
```

A 10R_pSJ6074 gene cat gene translationally coupled construct was prepared by assembling, in a SOE PCR reaction, the cat gene fragment amplified from pDN1050 DNA using primers (SEQ ID NO: 9) and (SEQ ID NO: 10), (Example 2, D)), with the 10R_pSJ6074 gene segment amplified from pSJ6074 DNA using primers (SEQ ID NO: 11) and (SEQ ID NO: 20), above, using primers (SEQ ID NO: 11) and (SEQ ID NO: 10) and an annealing temperature of 65° C. for amplification of the final SOE construct. This final SOE construct was then digested with BamHI+MluI, and the 0.75 kb fragment was ligated to the 4.35 kb MluI-BamHI fragment of pSJ6074, thus replacing the 3' end of the 10R_pSJ6074 gene in pSJ6074 with the 3' end translationally coupled to the cat gene. The ligation mixture was transformed into *E. coli* SJ2, and a transformant, which had a single basepair substitution in the region between the 10R stop codon and the cat gene start codon, as well as a silent mutation within the cat coding region, was kept as SJ8848 (SJ2/pSJ8848).

Plasmid pSJ8848 was transformed into *E. coli* SJ388 (a dam– strain), and two transformants kept as SJ8863 (SJ388/pSJ8848) and SJ8864 (SJ388/pSJ8848). Finally, a 2.5 kb EcoRI-BclI fragment containing the cryIIIA_stab segment, the 10R_pSJ6074 gene sequence, and the cat gene, was excised and purified from pSJ8848 extracted from the dam– host.

The final DNA construct used for transformation of *B. subtilis* was prepared by ligation of the following four fragments:

A SphI-BglII fragment prepared as described in Example 2, A), containing "pel_upstream+res-spc-res". The fragment (4.4 kb) was excised from pSJ8729 and gel purified.

A BglII-EcoRI fragment prepared as described in Example 2, B), containing "Ptriple". The fragment (0.44 kb) was excised from pSJ8722 and gel purified.

The EcoRI-BclI fragment prepared as described under 5A), above, containing "cryIIIA_stab-10R synthetic gene-cat". The fragment (2.5 kb) was excised from pSJ8848 and gel purified.

A BamHI-SphI fragment prepared as described in Example 2, C), containing "pel_downstream". The fragment (2.3 kb) was excised from pSJ8724 and gel purified.

Initially, the 2.5 kb EcoRI-BclI fragment and the 2.3 kb BamHI-SphI fragment were mixed and ligated, the ligation mixture was then digested with EcoRI and SphI, the enzymes heat inactivated, the 4.4 kb SphI-BglII fragment and the 0.44 kb BglII-EcoRI fragment were added and the mixture ligated again, and this ligation mixture was subsequently used to transform competent cells of *B. subtilis* PL1801 to spectinomycin resistance (180 microgram/ml). By replica plating, more than 50% of the colonies appearing on the spectinomycin plates were found to be chloramphenicol resistant (to 6 microgram/ml), and to be protease positive on plates with skim milk. 2 such strains were kept as SJ8923 and SJ8924.

5B) Construction of a 10R_pSJ7802-cat Translationally Coupled Construct.

Several DNA fragments used in the strain constructions were prepared as described in Example 2, sections A), B), C), and D). In addition, the following fragments were used for the high yielding gene:

A 10R_pSJ7802 gene segment was amplified from pSJ7802 using the following primers and an annealing temperature of 65° C.:

Downstream reading primer #289358, near start of synthetic 10R genes (pos. 659-679 in pSJ7802):

```
(SEQ ID NO: 17):
5'-GACTAAGCTTCTGCAGCAGCGGCGGCTACTGGAGCATTACCTCAG
                                <- pSJ7802 659-679 ->
```

Upstream 10R_pSJ7802 gene SOE primer #542634 (pos. 1734-1711 in pSJ7802)

```
(SEQ ID NO: 21):
5'-CCAATTGTCTAAATCAATTTTATTAAAGTTCAtgccgctagcacgcg ttaTGTTCTA
<-complementary to SEQ ID NO: 9) -><-
pSJ7802 1734-1711 ->
```

The PCR amplified fragment was digested with MfeI+BamHI, and the 0.12 kb fragment gel purified. It was ligated to pSJ8847, which had been digested with MfeI+BamHI, and subsequently treated with alkaline phosphatase. The ligation mixture was transformed into *E. coli* SJ388, and two transformants, having the correct DNA sequence of the PCR amplified segment, were kept as SJ8966 (SJ388/pSJ8966) and SJ8967 (SJ388/pSJ8967).

The final translationally coupled DNA construct used for transformation of *B. subtilis* was prepared by ligation of the following four fragments:

A SphI-BglII fragment containing "pel_upstream+res-spc-res". The fragment (4.4 kb) was excised from pSJ8881 and gel purified.

A BglII-EcoRI fragment containing "Ptriple". The fragment (0.44 kb) was excised from pSJ8722 and gel purified.

The EcoRI-BclI fragment containing "cryIIIA_stab-10R synthetic gene-cat". The fragment (2.5 kb) was excised from pSJ8966 and gel purified.

A BamHI-SphI fragment containing "pel_downstream". The fragment (2.3 kb) was excised from pSJ8724 and gel purified.

Initially, the 2.5 kb EcoRI-BclI fragment and the 2.3 kb BamHI-SphI fragment were mixed and ligated, the ligation mixture was then digested with EcoRI and SphI, and the 4.8 kb fragment gel purified. The 4.4 kb SphI-BglII fragment and the 0.44 kb BglII-EcoRI fragment were added and the mixture ligated, and this ligation mixture was subsequently used to transform competent cells of *B. subtilis* PL1801 to spectinomycin resistance (180 microgram/ml). By replica plating, more than 50% of the colonies appearing on the spectinomycin plates were found to be chloramphenicol resistant (to 6 microgram/ml), to be protease positive on plates with skim milk, and to be devoid of pectate lyase activity, by a plate assay, confirming that they were obtained by a double homologous recombination event. 2 such strains were kept as SJ8986 and SJ8987.

Example 6

10R Protease Yield and Chloramphenicol Resistance Determination

*Bacillus subtilis* strains containing the translationally coupled protease 10R-cat gene constructs were fermented in 500 ml shake flasks containing 100 ml PS-1 medium. Each strain was resuspended in a small volume of TY medium, and aliquots used to inoculate 5 shake flasks for each strain. These were incubated at 300 rpm for 5 days at 30° C., and culture broth analyzed for protease activity, with the following results:

TABLE 1

| Strain | Average protease yield, units/ml | Standard deviation |
|---|---|---|
| SJ8919 (4 bp spacing; 10R_pSJ6074) | 179 | 16 |
| SJ8920 (4 bp spacing; 10R_pSJ6074) | 157 | 18 |
| SJ8984 (4 bp spacing; 10R_pSJ7802) | 579 | 153 |
| SJ8985 (4 bp spacing; 10R_pSJ7802) | 614 | 71 |
| SJ8923 (14 bp spacing; 10R_pSJ6074) | 232 | 23 |
| SJ8924 (14 bp spacing; 10R_pSJ6074) | 214 | 52 |
| SJ8986 (14 bp spacing; 10R_pSJ7802) | 539 | 74 |
| SJ8987 (14 bp spacing; 10R_pSJ7802) | 520 | 67 |

The SJ8920 result is based on 4 flasks only, as one flask had obviously failed to ferment properly (yield 20 units/ml).

It is evident from the results in table 1, that strains containing the 10R_pSJ7802 synthetic gene are significantly higher yielding than strains containing the 10R_pSJ6074 synthetic gene.

The chloramphenicol resistance phenotype was determined by plating on LB plates supplemented with phosphate (0.01 M K3PO4), glucose (0.4%), skimmed milk (1%), and chloramphenicol at various concentrations.

Each strain was resuspended in a small volume of TY medium, and a 1 microliter inoculation loop was used to streak from this suspension onto the plates; each strain was streaked 5 times on each plate.

The plates were incubated at 37° C. overnight, and photographs taken the next day, it is evident that the strains containing the high-yielding synthetic 10R protease gene are significantly more chloramphenicol resistant that the otherwise isogenic strains containing the low-yielding synthetic gene.

Example 7

Construction of Bacillus licheniformis Strains Containing Translationally Coupled Selection Construct for Synthetic 10R Genes with a Spacing of 4 bp As a host strain for demonstration of the use of translational coupling to the chloramphenicol resistance gene as a means of selection for highly expressed synthetic genes was used strain SJ8071, described in PCT/EP2007/055190 (Novozymes NS, filed on 29 May 2007). This strain has a deletion of a chromosomal chloramphenicol resistance gene, making it a preferred host for experiments involving chloramphenicol resistance.

Fragments containing cryIIIA_stab-10R synthetic gene-cat-amyL_term were excised from either pSJ8846 (containing the 10R_pSJ6074 gene) or from pSJ8964 (containing the 10R_pSJ7802 gene) as 2.5 kb EcoRI-HindIII fragments. Each fragment was ligated to the 4.6 kb HindIII-EcoRI fragment from pSJ5487 (described in WO 2005/123915), and the ligation mixture transformed into PL1801 competent cells. 2 correct transformants with each construct were kept, SJ9074 and SJ9075 containing plasmids pSJ9074 and pSJ9075 with the 10R_pSJ6074 gene, and SJ9076 and SJ9077 containing plasmids pSJ9076 and pSJ9077 with the 10R_pSJ7802 gene. These plasmids contain, on a temperature sensitive replicon conferring erythromycin resistance, the cryIIIA_stab-10R synthetic gene-cat-amyL_term followed by a segment from the chromosomal amyL region downstream of the amyL gene in *B. licheniformis*. The *B. licheniformis* host strain has a promoter region, including the cryIIIA_stab segment (the triple promoter region described in WO 2005/123915), reading into the alpha-amylase gene, which is followed by the segment from the chromosomal amyL region downstream of the amyL gene, which is also present on the introduced plasmids. A double homologous recombination event between the introduced plasmid and the chromosome, at cryIIIA_stab and the downstream amyL segment, will lead to replacement of the alpha-amylase gene with the translationally coupled 10R-cat construct, which will then be under control of the triple promoter region.

These plasmids were subsequently transformed into competent cells of *B. subtilis* strain PP289-5 (U.S. Pat. No. 6,066,473), resulting in SJ9083 and SJ9084 (with pSJ9074), SJ9085 and SJ9086 (with pSJ9075), SJ9087 and SJ9088 (with pSJ9076), and SJ9089 and SJ9090 (with pSJ9077).

Conjugations were performed essentially as described in U.S. Pat. No. 6,066,473, selecting for erythromycin resistance. Tetracycline sensitive transconjugants were isolated, and amylase negative and erythromycin sensitive strains were isolated following integration and excision of the deletion plasmid.

Transconjugants were streaked onto LB plates supplemented with phosphate (0.01 M K3PO4), glucose (0.4%), starch (0.5%) and erythromycin (5 microgram/ml) which were incubated at 50° C. overnight. The selection for erythromycin resistance at high temperature ensures that colonies formed have arisen by integration of the plasmid into the *B. licheniformis* host strain chromosome by homologous recombination at either the cryIIIA_stab or the downstream amyL sequence, because the plasmid is unable to replicate as a free plasmid at this temperature. Amylase negative colonies were reisolated several times on LB plates supplemented with phosphate (0.01 M K3PO4), glucose (0.4%), and skimmed milk (1%) at 30° C., to allow the replication of the integrated plasmid, which facilitates its excision from the chromosome, and ultimately loss from the cell (indicated by erythromycin sensitivity). Amylase negative, protease positive and erythromycin sensitive colonies were subsequently detected by replica plating.

Strains containing the chromosomally integrated, translationally coupled 10R-cat constructs were obtained from each of the conjugative donor strains and named isolate 1 to isolate 8. Isolates 2 and 4 were kept as SJ9150 and SJ9151, containing the 10R_pSJ6074 gene, and isolates 6 and 8 were kept as SJ9152 and SJ9153, respectively, containing the 10R_pSJ7802 gene.

Example 8

10R Protease Yield and Chloramphenicol Resistance Determination of *B. licheniformis* Strains from Example 7

*Bacillus licheniformis* strains containing the translationally coupled protease 10R-cat gene constructs of example 7 were fermented in 500 ml shake flasks containing 100 ml PS-1 medium. Each strain was resuspended in a small volume of TY medium, and aliquots used to inoculate 2 shake flasks for each strain. These were incubated at 300 rpm for 5 days at 30° C., and culture broth analyzed for protease activity, with the following results:

TABLE 2

| Strain | | Average protease yield, units/ml |
|---|---|---|
| Isolate 1 | (10R_pSJ6074) | 67 |
| Isolate 2 = SJ9150 | (10R_pSJ6074) | 37 |
| Isolate 3 | (10R_pSJ6074) | 36 |
| Isolate 4 = SJ9151 | (10R_pSJ6074) | 49 |
| Isolate 5 | (10R_pSJ7802) | 483 |
| Isolate 6 = SJ9152 | (10R_pSJ7802) | 642 |
| Isolate 7 | (10R_pSJ7802) | 543 |
| Isolate 8 = SJ9153 | (10R_pSJ7802) | 706 |

It is evident from the results in table 2, that strains containing the 10R_pSJ7802 synthetic gene, i.e. strains SJ9152 and SJ9153, are significantly higher yielding than strains containing the 10R_pSJ6074 synthetic gene.

The chloramphenicol resistance phenotype was determined by plating on LB plates supplemented with phosphate (0.01 M K3PO4), glucose (0.4%), skimmed milk (1%), and chloramphenicol at various concentrations. Each strain was resuspended in a small volume of TY medium, and a 1 microliter inoculation loop was used to streak from this suspension onto the plates; each strain was streaked 5 times on each plate.

Figure 4:
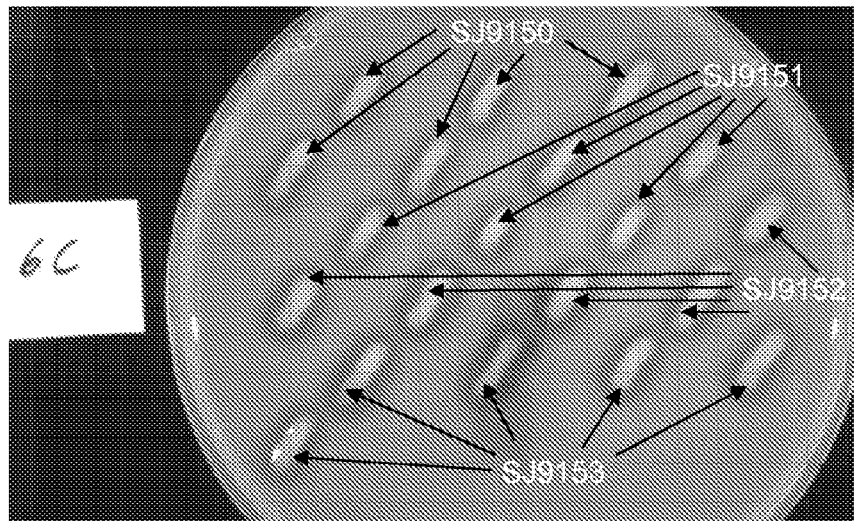
FIG. 4 shows testing of the 4 bp constructs from example 8. The labelling is interpreted as follows: "6C" indicates that the plate contains 6 microgram/ml chloramphenicol, "400" indicates it contains 40 microgram/ml chloramphenicol, and "800" contains 80 microgram/ml chloramphenicol. It is evident that the strains containing the high-yielding synthetic 10R protease gene (10R_pSJ7802), i.e. strains SJ9152 and SJ9153, are significantly more chloramphenicol resistant that the otherwise isogenic strains containing the low-yielding synthetic gene (10R_pSJ6074).
Figure 4:
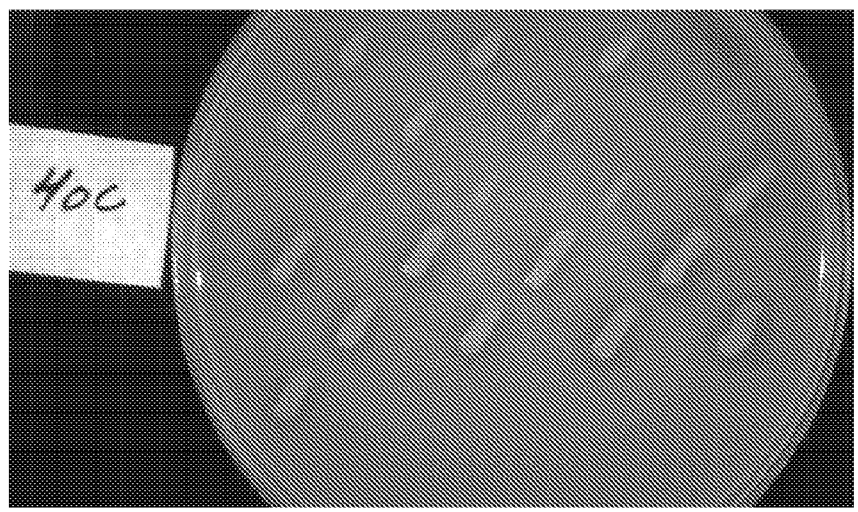
Figure 4:
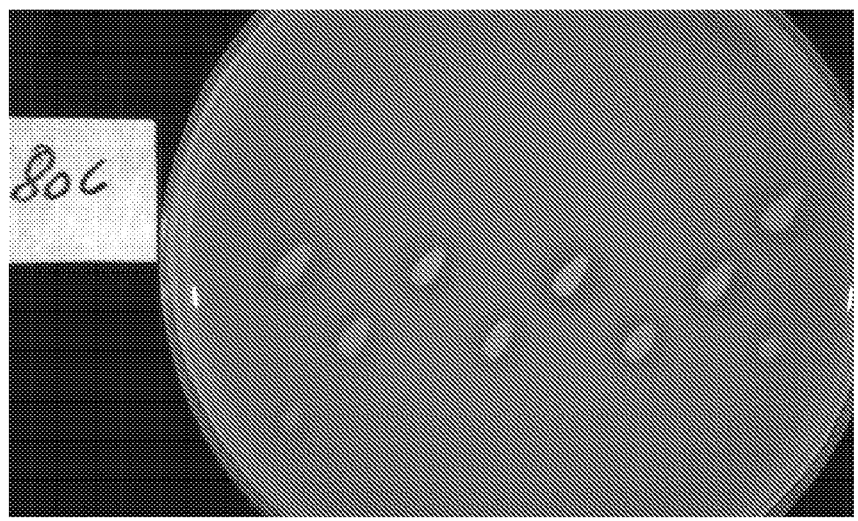

The plates were incubated at 37° C. overnight, and photographs taken the next day. It is evident that the strains containing the high-yielding synthetic 10R protease gene (10R_pSJ7802), i.e. strains SJ9152 and SJ9153, are significantly more chloramphenicol resistant that the otherwise isogenic strains containing the low-yielding synthetic gene (10R_pSJ6074). See FIG. 4.

Example 9

Construction of a Library of Synthetic 10R Gene Sequences Translationally Coupled to a cat Gene with a Spacing of 4 Basepairs As a test of the selection principle, a construct was designed in which a library of synthetic 10R gene sequences, with variation introduced within the last 50 basepairs of the 10R coding sequence, was translationally coupled to the pC194-derived cat gene.

The translational coupling setup was such that the stop codon for any variant of the synthetic 10R gene (TAA) was followed by a 4 bp region (CGCG), which again was followed by the start codon for the cat gene (ATG).

The following degenerate primer #550951 was designed for making the intended variation

```
(SEQ ID NO: 22):
5'-CCAATTGTCTAAATCAATTTTATTAAAGTTCATCGCGTTATGTNCGN

AGNCGNA - (cont.)
< complementary to SEQ ID No: 9 ->

(cont.) -CNCCCCANGARTTNACCATNGGNGTNACYTCYTGGTAGAAC

GTTGTGCCACCTG
                            < pSJ6074 pos.2067-2046
``` wherein the symbols have the following meaning:

| Symbol | Meaning |
|---|---|
| R | A or G |
| Y | C or T |
| N | A or C or G or T |

Plasmid pSJ6074 was used as template in a PCR amplification with the following primers:

Downstream reading primer #289358, near start of synthetic 10R genes (pos. 1055-1075 in pSJ6074)

```
(SEQ ID NO: 17):
5'-GACTAAGCTTCTGCAGCAGCGGCGGCTACTGGAGCATTACCTCAG
                        <- pSJ6074 1055-1075 ->
``` and the above primer #550951 (SEQ ID NO:22).

A library of different synthetic 10R genes each translationally coupled to the cat gene was prepared by assembling, in a SOE PCR reaction, the cat gene fragment amplified from pDN1050 DNA using primers (SEQ ID NO: 9) and (SEQ ID NO: 10), (Example 2, D)), with the 10R_pSJ6074 gene segment amplified from pSJ6074 DNA using primers (SEQ ID NO: 17) and (SEQ ID NO:22), above, using primers (SEQ ID NO: 17) and (SEQ ID NO: 10) and an annealing temperature of 45° C. for amplification of the final SOE construct. The final SOE construct was then digested with MfeI and BamHI, and the 124 bp fragment gel purified. The fragment was ligated to the gel purified 5004 bp MfeI-BamHI fragment of pSJ8847 (described above, in example 4, 4B); this fragment had been treated with alkaline phosphatase), and the ligation mixture transformed into the dam⁻ strain *E. coli* SJ388 bp electroporation, selecting ampicillin resistance.

The transformant colonies (a few hundred) were scraped off the plate and the mixture used to inoculate a liquid TY culture containing ampicillin, which was propagated for 6 hours at 37° C., whereafter this was harvested and plasmids extracted. An aliquot of this mixed plasmid preparation was digested with BclI and EcoRI, and the 2.5 kb fragment gel purified.

The final translationally coupled DNA library construct used for transformation of *B. subtilis* was prepared by ligation of the following four fragments:

A SphI-BglII fragment containing "pel_upstream+res-spc-res". The fragment (4.4 kb) was excised from pSJ8881 and gel purified.

A BglII-EcoRI fragment containing "Ptriple". The fragment (0.44 kb) was excised from pSJ8722 and gel purified.

The EcoRI-BclI fragment containing "cryIIIA_stab-10R synthetic gene library-cat". This fragment (2.5 kb) was excised from the mixed plasmid preparation as described above.

A BamHI-SphI fragment containing "pel_downstream". The fragment (2.3 kb) was excised from pSJ8724 and gel purified.

Initially, the 2.5 kb EcoRI-BclI fragment and the 2.3 kb BamHI-SphI fragment were mixed and ligated, the ligation mixture was then digested with EcoRI and SphI, and the 4.8 kb fragment gel purified. The 4.4 kb SphI-BglII fragment and the 0.44 kb BglII-EcoRI fragment were added and the mixture ligated, and this ligation mixture was subsequently used to transform competent cells of *B. subtilis* PL1801 to spectinomycin resistance (180 microgram/ml).

The spectinomycin plate with transformants was replica plated onto 1) a spectinomycin plate with skim milk, 2) a plate with 6 microgram/ml chloramphenicol, 3) a plate with 6 microgram/ml chloramphenicol and skim milk, and 4) a plate with 100 microgram/ml chloramphenicol.

Approximately half of all colonies were protease-positive, and all protease-positive colonies were chloramphenicol resistant. Colonies were picked from various plates as follows: 10 at random from the plate with 6 microgram/ml chloramphenicol; 10 at random from the plate with 100 microgram/ml chloramphenicol; 6 particularly large colonies from the plate with 100 microgram/ml chloramphenicol; and 17 colonies from the plate with 6 microgram/ml chloramphenicol, that did not grow on the plate with 100 microgram/ml chloramphenicol.

A DNA fragment spanning the region of the 10R gene, in which variation was introduced, was PCR amplified from each of these colonies, using primers #410250 and #538513, and the DNA sequence of the BamHI-MfeI segment determined using primer #519847.

Primer #410250 (SEQ ID NO:23):

(SEQ ID NO: 23):   5'-CACGATGGGTGGTCGCTGCAGC

Primer #538513 (SEQ ID NO:24):

(SEQ ID NO: 24):   5'-GTCGTTTGTTGGTTCAAATAATG

Downstream reading primer #519847, upstream BamHI site (pos. 1907-1931 in pSJ6074): (SEQ ID NO: 11)

5'-AGCGTGAGCTATCCTGAAGGTACCG        (SEQ ID NO: 11)

A large number of colonies were found to contain undesired mutations, that either changed the 10R amino acid sequence, or changed nucleotides downstream from the stop codon or in the cat gene, and three pairs of clones had identical sequences. 13 Unique, correct strains selected for further characterization were kept as SJ9019, SJ9020, SJ9021, SJ9028, SJ9030, SJ9032, SJ9033, SJ9037, SJ9044, SJ9047, SJ9054, SJ9057, and SJ9059. Their DNA sequences in the variable region were as shown in table 3.

TABLE 3

DNA sequences in the variable regions of the 10R gene in 13 selected strains.

```
pSJ6074 (SEQ ID NO: 25)   A C C A G G A A G T G A C A C C G A T G G T G A A

SJ9019 (SEQ ID NO: 26)    A C C A G G A G G T G A C C C C T A T G G T A A A
SJ9020 (SEQ ID NO: 27)    A C C A G G A A G T C A C T C C T A T G G T G A A
SJ9021 (SEQ ID NO: 28)    A C C A A G A A G T G A C G C C A A T G G T G A A
SJ9028 (SEQ ID NO: 29)    A C C A A G A A G T A A C G C C T A T G G T T A A
SJ9030 (SEQ ID NO: 30)    A C C A A G A G G T T A C T C C A A T G G T A A A
SJ9032 (SEQ ID NO: 31)    A C C A G G A A G T A A C C C C a t G G t T A A
SJ9033 (SEQ ID NO: 32)    A C C A G G A A G T C A C G C C T A T G G T T A A
SJ9037 (SEQ ID NO: 33)    A C C A A G A A G T G A C T C C A A T G G T A A A
SJ9044 (SEQ ID NO: 34)    A C C A G G A A G T T A C A C C C A T G G T C A A
SJ9047 (SEQ ID NO: 35)    A C C A A G A G G T A A C G C C T A T G G T T A A
SJ9054 (SEQ ID NO: 36)    A C C A A G A G G T T A C T C C A T G G T A A A
SJ9057 (SEQ ID NO: 37)    A C C A A G A G G T C A C C C C A A T G G T T A A
SJ9059 (SEQ ID NO: 38)    A C C A A G A G G T G A C T C C T A T G G T T A A

Primer, complementary
(SEQ ID NO: 39) 5'        T G G T Y C T Y C A N T G N G G N T A C C A N T T 3'                        A C C A R G A R G T N A C N C C N A T G G T N A A
                          Gln   Glu   Val   Thr   Pro   Met   Val   Ile (pSJ6074)      C T C T T G G G G A G T T A G A C T C C G T A C a t a A (SJ9019)       C T C A T G G G G C G T G C G G C T A C G C A C A T A A
  (SJ9020)       C T C G T G G G G G G T C C G C C T C C G A A C A T A A
  (SJ9021)       C T C T T G G G G C G T T C G A C T C C G T A C A T A A
  (SJ9028)       C T C T T G G G G T G T T C G G C T A C G A A C A T A A
  (SJ9030)       C T C C T G G G G A G T G C G A C T C C G G A C A T A A
  (SJ9032)       C T C G T G G G G A G T G C G A C T C C G G A C A T A A
  (SJ9033)       C T C T T G G G G C G T T C G C C T T C G G A C A T A A
  (SJ9037)       T T C T T G G G G C G T T C G A C T T C G A A C A T A A
  (SJ9044)       C T C A T G G G G A G T C C G G C T T C N G A C A T A A
  (SJ9047)       T T C A T G G G G C G T C C G G C T G C G T A C A T A A
  (SJ9054)       C T C T T G G G G G G T C C G G C T G C G T A C A T A A
  (SJ9057)       T T C T T G G G G G G T C C G T C T T C G C A C A T A A
  (SJ9059)       C T C G T G G G G A G T T C G G C T C C G C A C A T A A (Primer)         R A G N A C C C C N C A N G C N G A N G C N T G T A T T Y T C N T G G G G N G T N C G N C T N C G N A C A T A A
                 Ser   Trp   Gly   Val   Arg   Leu   Arg   Thr   END
```

Example 10

10R Protease Yield and Chloramphenicol Resistance Determination

The 13 unique, correct strains isolated from the protease 10R gene library as described above in example 9 were characterized with respect to their chloramphenicol resistance phenotype, by plating on LB plates supplemented with phosphate (0.01 M K3PO4), glucose (0.4%), skimmed milk (1%), and chloramphenicol at various concentrations.

Each strain was resuspended in a small volume of TY medium, and a 1 microliter inoculation loop was used to streak from this suspension onto the plates; 3 plates were used in parallel for each chloramphenicol concentration, and each strain was streaked once on each plate. Plates with 6, 20, 40, 80, and 100 microgram/ml chloramphenicol were used.

Figure 5A:
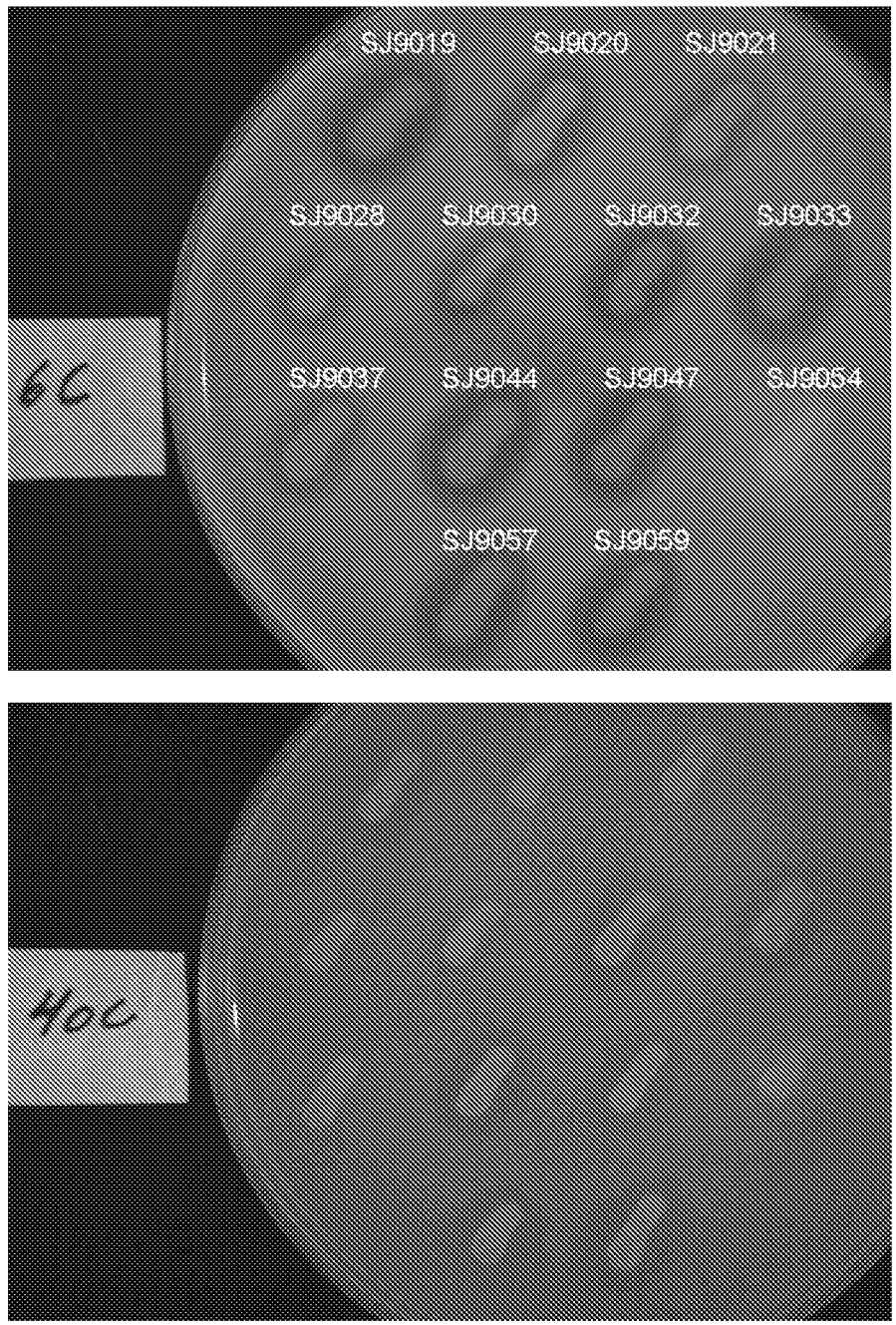
FIGS. 5A and 5B shows three representative plates from example 10, illustrating growth on 6, 40, and 100 microgram/ml chloramphenicol.
Figure 5B:
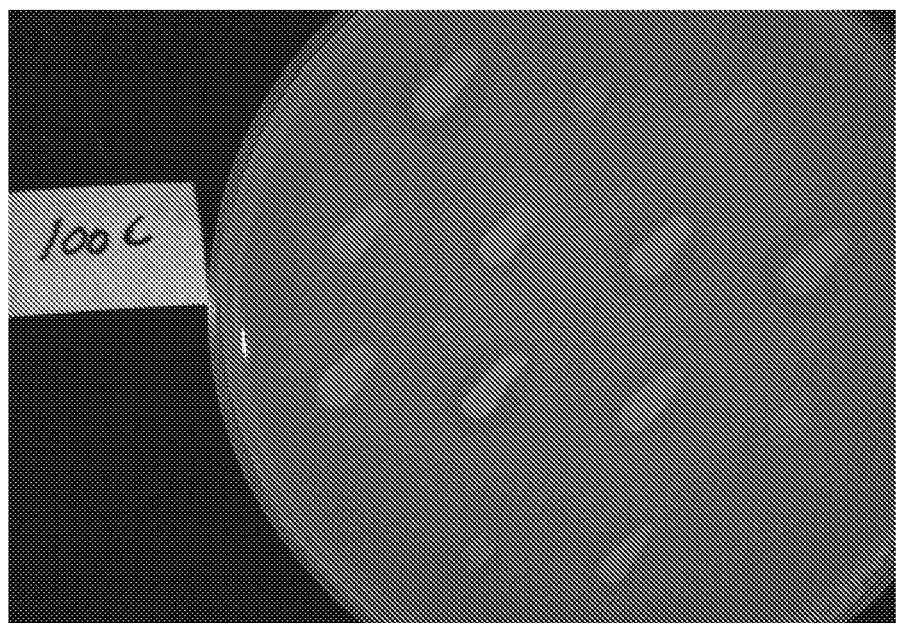
Figure 6:
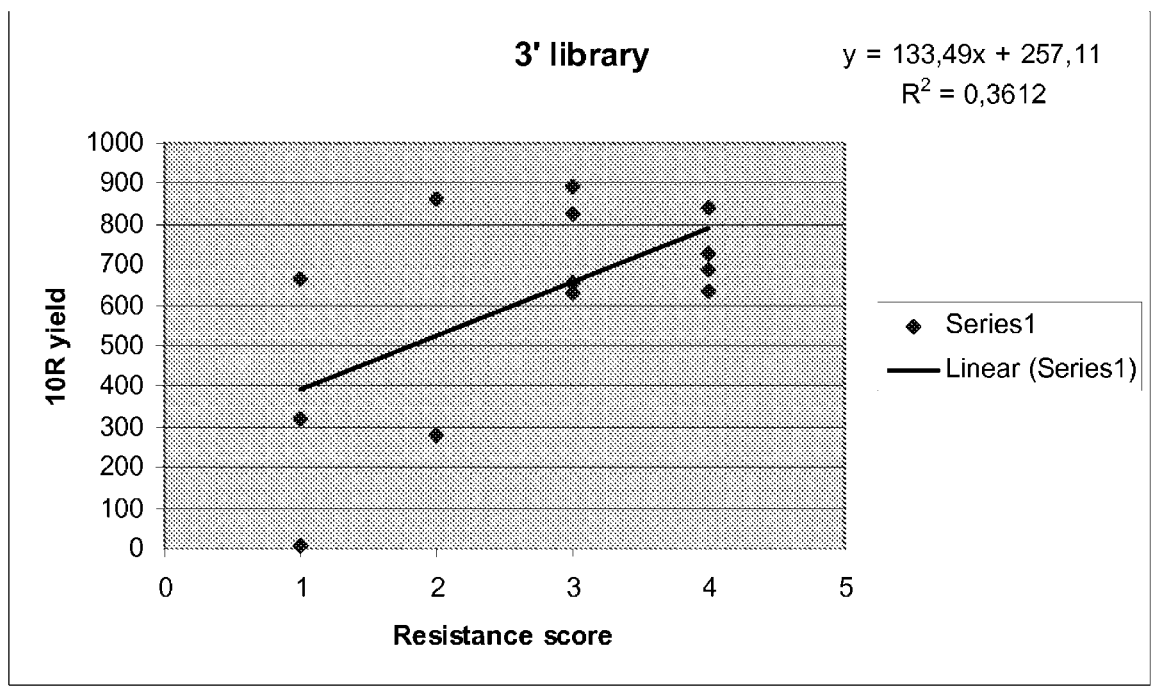
FIG. 6 illustrates the protease 10R yield depicted against the chloramphenicol resistance score. It appears that strains having a high chloramphenicol resistance score are consistently high-yielding with respect to protease 10R, whereas strains having a lower resistance score are showing a more variable protease 10R yield

The plates were incubated at 37° C. overnight, and photographs taken the next day. Three representative plates, illustrating growth on 6, 40, and 100 microgram/ml chloramphenicol, are shown in FIG. 5. Based on visual inspection of all plates, strains were given a score for chloramphenicol resistance from 1 (lowest level of resistance; very little growth at 100, and still affected at 20 microgram/ml chloramphenicol) to 4 (good growth at 80 and 100 microgram/ml chloramphenicol).

The TY suspension used above was also used to inoculate four 500 ml shake flasks containing 100 ml PS-1 medium for each strain. These were incubated at 300 rpm for 4 days at 30° C., and culture broth analyzed for protease activity.

The results of the protease yield and the chloramphenicol resistance determination are given in table 4.

TABLE 4

Protease yield and chloramphenicol resistance.

| SJ strain | 9019 | 9020 | 9021 | 9028 | 9030 | 9032 | 9033 |
|---|---|---|---|---|---|---|---|
| units/ml | 694 | 502 | 344 | 1053 | 895 | 729 | 583 |
| units/ml | 641 | 883 | 307 | 420 | 949 | 781 | 484 |
| units/ml | 678 | 738 | 272 | 932 | 862 | 708 | 663 |
| units/ml | 732 | 532 | 357 | 1033 | 856 | 684 | 805 |
| Resistance | 4 | 1 | 1 | 2 | 3 | 4 | 4 |
| Average yield | 686.25 | 663.75 | 320 | 859.5 | 890.5 | 725.5 | 633.75 |

| SJ strain | 9037 | 9044 | 9047 | 9054 | 9057 | 9059 |
|---|---|---|---|---|---|---|
| units/ml | 700 | 822 | 706 | 3 | 438 | 537 |
| units/ml | 980 | 722 | 708 | 3 | 271 | 615 |
| units/ml | 913 | 993 | 575 | 3 | 196 | 780 |
| units/ml | 714 | 818 | 536 | 4 | 208 | 696 |
| Resistance | 3 | 4 | 3 | 1 | 2 | 3 |
| Average yield | 826.75 | 838.75 | 631.25 | 3.25 | 278.25 | 657 |

FIG. 5 illustrates the protease 10R yield depicted against the chloramphenicol resistance score. It appears that strains having a high chloramphenicol resistance score are consistently high-yielding with respect to protease 10R, whereas strains having a lower resistance score are showing a more variable protease 10R yield.

---

The invention claimed is:

1. A method of screening for and/or selecting a recombinant prokaryotic host cell having an improved polypeptide production level, comprising:
 introducing at least two different open reading frames into prokaryotic host cells thereby providing an expression library, wherein
  (i) the at least two different open reading frames encode the same polypeptide,
  (ii) each of the at least two different open reading frames is translationally coupled to a downstream gene encoding a screenable or selectable reporter, and
  (iii) each of the at least two different open reading frames is integrated into the genome of a separate prokaryotic host cell;
 (b) culturing the prokaryotic host cells under conditions conducive to the expression of the polypeptide; and
 (c) screening for and/or selecting a prokaryotic host cell having an improved polypeptide production level of the translationally coupled reporter when compared to the other prokaryotic host cells, thereby identifying an open reading frame having an improved polypeptide production level in the host cell.

2. The method of claim 1, wherein the expression library comprises at least five different open reading frames.

3. The method of claim 1, wherein the expression library comprises at least 100 different open reading frames.

4. The method of claim 1, wherein the prokaryotic host cell is a Gram positive host cell.

5. The method of claim 4, wherein the Gram positive host cell is a *Bacillus* cell.

6. The method of claim 5, wherein the *Bacillus* cell is a *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, or *Bacillus thuringiensis* cell.

7. The method of claim 1, wherein the polypeptide is an enzyme.

8. The method of claim 7, wherein the enzyme is a lyase, a ligase, a hydrolase, an oxidoreductase, a transferase, or an isomerase.

9. The method of claim 8, wherein the enzyme is selected from the group consisting of an amylolytic enzyme, a lipolytic enzyme, a proteolytic enzyme, an oxidoreductase and a plant cell-wall degrading enzyme.

10. The method of claim 7, wherein the enzyme has an activity selected from the group consisting of aminopeptidase, amylase, amyloglucosidase, carbohydrase, carboxypeptidase, catalase, cellulase, chitinase, cutinase, cyclodextrin glycotransferase, deozyribinuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinase, peroxidase, phytase, phenoloxidase, polyphenoloxidase, protease, ribonuclease, transferase, transglutaminase, and xylanase.

11. The method of claim 1, wherein each of the at least two different open reading frames is site-specifically integrated into the same locus of each host cell.

12. The method of claim 1, wherein each of the at least two different open reading frames is transcribed from at least one heterologous promoter.

13. The method of claim 12, wherein at least one heterologous promoter comprises an artificial promoter.

14. The method of claim 13, wherein the artificial promoter comprises one or more mRNA-stabilizing sequence.

15. The method of claim 1, wherein the screenable or selectable reporter provides an antibiotic resistance to the host cell.

16. The method of claim 1, wherein the gene encoding a screenable or selectable reporter is optimized for expression in said host cell.

17. The method of claim 1, wherein each of the at least two different open reading frames is translationally coupled to the downstream gene encoding the screenable or selectable reporter such that the start codon of the reporter gene is no more than 500 by downstream of the stop-codon of the polypeptide encoding open reading frame.

18. The method of claim 17, wherein each of the at least two different open reading frames is translationally coupled to the downstream gene encoding the screenable or selectable reporter such that the start codon of the reporter gene overlaps with the stop-codon of the polypeptide encoding open reading frame.

19. The method of claim 18, wherein each of the at least two different open reading frames is translationally coupled to the downstream gene encoding the screenable or selectable reporter such that the start codon of the reporter gene overlaps with the stop-codon of the polypeptide encoding open reading frame, as follows: ATGA, wherein the stop-codon is underscored and the start-codon is bold.

* * * * *

UNITED STATES PATENT AND TRADEMARK OFFICE
CERTIFICATE OF CORRECTION

| | | |
|---|---|---|
| PATENT NO. | : 9,334,493 B2 | Page 1 of 1 |
| APPLICATION NO. | : 12/516721 | |
| DATED | : May 10, 2016 | |
| INVENTOR(S) | : Joergensen et al. | |

It is certified that error appears in the above-identified patent and that said Letters Patent is hereby corrected as shown below:

Claims

In claim 1, line 4 at column 53, line 15, before "introducing", insert -- (a) --.

In claim 10, line 5 at column 54, line 15, delete "deozyribinuclease" and insert -- deoxyribonuclease --.

Signed and Sealed this
Twenty-third Day of August, 2016

Michelle K. Lee
*Director of the United States Patent and Trademark Office*